(12) United States Patent
Ben-Shmuel et al.

(10) Patent No.: US 8,945,428 B2
(45) Date of Patent: Feb. 3, 2015

(54) DEVICE AND METHOD OF SANITATION AND/OR STERILIZATION

(75) Inventors: Eran Ben-Shmuel, Ganei Tikva (IL); Alexander Bilchinsky, Monosson-Yahud (IL); Steven R. Rogers, D. N. Emek Sorek (IL); Daniella Atzmony, Shoham (IL); Elliad Silcoff, Tel Aviv (IL)

(73) Assignee: Goji Limited, Hamilton (BM)

( * ) Notice: Subject to any disclaimer, the term of this patent is extended or adjusted under 35 U.S.C. 154(b) by 321 days.

(21) Appl. No.: 13/394,531

(22) PCT Filed: Sep. 7, 2010
(Under 37 CFR 1.47)

(86) PCT No.: PCT/US2010/047968
§ 371 (c)(1),
(2), (4) Date: Jan. 15, 2013

(87) PCT Pub. No.: WO2011/029089
PCT Pub. Date: Mar. 10, 2011

(65) Prior Publication Data
US 2013/0171023 A1    Jul. 4, 2013

Related U.S. Application Data

(60) Provisional application No. 61/240,267, filed on Sep. 7, 2009, provisional application No. 61/315,040, filed on Mar. 18, 2010.

(51) Int. Cl.
*H01B 1/00* (2006.01)
*F21V 9/00* (2006.01)
*C01D 17/00* (2006.01)
(Continued)

(52) U.S. Cl.
CPC ............. *C01D 17/00* (2013.01); *A47L 15/4236* (2013.01); *C11D 3/046* (2013.01);
(Continued)

(58) Field of Classification Search
CPC .................................... A61L 2/00; A61L 9/18
USPC .......... 422/1, 28, 292; 134/1, 6; 252/500, 582
See application file for complete search history.

(56) References Cited

U.S. PATENT DOCUMENTS 4,670,306 A    6/1987  Salem
5,236,512 A    8/1993  Rogers et al.
(Continued)

FOREIGN PATENT DOCUMENTS

DE           1610307        4/1971
WO      WO 97/29016 A1     8/1997
(Continued)

OTHER PUBLICATIONS

International Search Report from the US Patent Office for International Application No. PCT/US2010/047968, mailed Nov. 5, 2010.

*Primary Examiner* — Monzer R Chorbaji
(74) *Attorney, Agent, or Firm* — Smith Risley Tempel Santos LLC; Patrick D. Lowder; Gregory Scott Smith

(57) ABSTRACT

A device for washing, sanitizing, and/or sterilizing an item is disclosed. The device may comprise a solution applicator for coating a surface of said item with a washing, sanitizing and/or sterilizing solution. The device may also comprise a heating unit for heating the solution coated on the surface of said item to a working temperature. The device may further comprise a control unit for keeping the temperature of the treating substance at the working temperature for a predetermined amount of time.

14 Claims, 5 Drawing Sheets

(51) Int. Cl.
*A47L 15/42* (2006.01)
*C11D 3/04* (2006.01)
*C11D 3/08* (2006.01)
*C11D 3/10* (2006.01)
*C11D 3/12* (2006.01)
*C11D 3/20* (2006.01)
*C11D 3/37* (2006.01)
*C11D 3/43* (2006.01)
*C11D 11/00* (2006.01)
*A61L 2/04* (2006.01)
*A61L 2/06* (2006.01)

(52) U.S. Cl.
CPC . *C11D 3/08* (2013.01); *C11D 3/10* (2013.01); *C11D 3/12* (2013.01); *C11D 3/1213* (2013.01); *C11D 3/1253* (2013.01); *C11D 3/2093* (2013.01); *C11D 3/3707* (2013.01); *C11D 3/43* (2013.01); *C11D 11/007* (2013.01); *A47L 15/42* (2013.01); *A61L 2/04* (2013.01); *A61L 2/06* (2013.01)
USPC .......................................... 252/500; 252/582

(56) References Cited

U.S. PATENT DOCUMENTS

| | | | |
|---|---|---|---|
| 5,882,739 A * | 3/1999 | Kobos et al. | 427/536 |
| 6,037,014 A | 3/2000 | Edgington | |
| 6,537,459 B1 | 3/2003 | Segaard | |
| 6,689,305 B1 | 2/2004 | Fernholz et al. | |
| 2003/0113529 A1 * | 6/2003 | Gibson et al. | 428/304.4 |
| 2004/0265500 A1 | 12/2004 | Kucera et al. | |
| 2005/0119153 A1 | 6/2005 | Burt et al. | |
| 2006/0278254 A1 * | 12/2006 | Jackson | 134/21 |
| 2007/0154527 A1 * | 7/2007 | Myers et al. | 424/443 |
| 2010/0132735 A1 | 6/2010 | Gaus et al. | |
| 2010/0139690 A1 | 6/2010 | Gaus et al. | |

FOREIGN PATENT DOCUMENTS

| | | |
|---|---|---|
| WO | WO 2008145213 A1 | 12/2008 |
| WO | WO 2008145214 A1 | 12/2008 |
| WO | WO 2008145216 A1 | 12/2008 |
| WO | WO 2008145217 A1 | 12/2008 |

* cited by examiner

DEVICE AND METHOD OF SANITATION AND/OR STERILIZATION

PRIORITY

Cross Reference to Related Applications

This application is a U.S. national phase application based on PCT/US2010/047968, filed Sep. 7, 2010, and claims the benefit of U.S. Provisional Application No. 61/240,264, filed Sep. 7, 2009, and U.S. Provisional Application No. 61/315,040, filed Mar. 18, 2010, the contents of all of which are incorporated by reference herein in their entirety.

FIELD AND BACKGROUND

The present disclosure, in some embodiments thereof, relates to sanitizing and/or sterilizing items and, more particularly, but not exclusively, relates to sanitizing food utensils, such as kitchenware, dinnerware, food storage containers, liquid-holding containers, and other items used with products suitable for human consumption.

Sanitation may include the hygienic means of promoting health through prevention of human contact with the hazards of wastes. For example, sanitation may refer to the adequate treatment of food-contact surfaces, such as surfaces of eating utensils, food packages, and the like, by a process that effectively destroys vegetative cells of microorganisms of public health significance, and substantially reduces numbers of other undesirable microorganisms, without adversely affecting the product or its safety for the consumer.

Sterilization is a process that eliminates, removes, or kills all forms of life, such as transmissible agents (e.g., fungi, bacteria, viruses, spore forms, etc.) present, for example, on a surface. Sterilization can be achieved, for example, by applying the proper combinations of heat, chemicals, irradiation, high pressure, and filtration.

SUMMARY

An aspect of some embodiments of the presently disclosed technology concerns sanitizing and/or sterilizing a surface of a dish or other item with radio frequency (RF) radiation. The item to be sanitized or sterilized may be made, for example, of plastic, clay, glass, and/or metal. The sanitization and/or sterilization may be carried out by first applying a treating substance to the surface and then heating the treating substance by RF radiation at least to a required temperature for a required period. For example, The British Norm BS2745 (washer disinfectors for medical purpose) describes a ware wash process with an included thermal sanitizing process as follows: the surface of the item processed should reach a minimum temperature of 71° C. for 3 minutes, 80° C. for 1 minute, 85° C. for 30 seconds, or 90° C. for 1 second. According to EN ISO 15883-1, sanitation requires heating the item surface to 80° C. for 30 seconds, 85° C. for 10 seconds, or 90° C. for 3 seconds. Thus, the required temperature and time depend on the applicable sanitation standard. Each such temperature-duration pair may provide a required temperature and a required period of time. Similarly, depending on the applicable sterilization standard, sterilization is achieved after heating the item surface to 180° C. for 9 seconds, 121° C. for 15 minutes, or 134° C. for 3 minutes.

The treating substance may be applied to the surface such that the treating substance creates a layer on the surface. The average thickness of that layer may remain substantially constant as long as the heating target (e.g. sterilization or sanitization) is not achieved. In some embodiments, the thickness of the layer remains substantially constant after the heating target is achieved, for example, after being at or above the required temperature for the required amount of time.

In some embodiments, the average thickness of a layer is considered to remain substantially constant if the deviation is no more than 25%, preferably no more than 10%. Consistent with some embodiments, the average thickness of layer is considered to remain substantially constant as long as it does not fall below a thickness threshold that is required to provide efficient RF heating. For example, the thickness threshold may be 1 mm, 0.5 mm, or 0.2 mm.

Retaining a layer of constant average thickness may be achieved, for example, by using a treating substance that is sufficiently viscous to stay on the surface at the required temperature for the required time, without significant substance flowing off the surface. Preferably, the treating substance also may exhibit sufficiently low surface energy to form a film on the item to be sanitized/sterilized.

Generally, retaining a layer of sufficient thickness for sufficient periods requires that the viscosity of the treating substance at about 40° C. is at least about 30 cS. In some embodiments, the viscosity of the treating substance may be about 50 cS, or at least about 100 cS. The higher the viscosity value is, the slower the substance may flow off the surface.

In some embodiments, after achieving the heating target, the viscosity of the treating substance may drop to a level that is sufficiently low such that the substance may flow off the surface. For example, viscosity may fall below 15 cS, sometimes below 10 cS, or sometimes below 5 cS.

In some embodiments, when the heating target is achieved, the viscosity of the treating substance decreases such that the treating substance flows off the surface. In some embodiments, flowing off minimizes or eliminates the need to rinse the treating substance. In some embodiments, after heating to the required temperature for sufficient time, the treating substance is washed away, for example, with clean water.

In some embodiments, after the item is held at the required temperature for sufficient time, it is further heated to cause the treating substance to flow off the item. In such embodiments, the viscosity of the treating substance at the required temperature may be higher than in embodiments that do not utilize further heating for removing the treating substance from the surface.

In some embodiments, the treating substance may first be heated to a temperature where it is sufficiently fluid to be sprayed onto the surface. The contact with the surface optionally cools the treating substance to a temperature at which the treating substance retains substantially constant layer thickness, for example, due to viscosity increase associated with the cooling. Then the treating substance may be heated to sanitize or sterilize the surface. Optionally, the treating substance may be further heated to reduce the viscosity of the treating substance, such that the treating substance flows off the surface.

In some embodiments, the treating substance may include a solid and be applied, for example, as an aerosol. In some embodiments, the solid may be applied on a wet item. For example, the item to be heated is first "wetted" by a solvent, and then a powder or aerosol is scattered or sprayed on the item, such that together with the solvent, a treating substance that clings to the surface may be obtained. Optionally, such treating substance drips off when the treating substance is sufficiently hot. The term "wetted" is used herein to describe contacts with any liquid, and not necessarily with water.

In some embodiments, the treating substance is applied as vapor. Applying vapor to the surface may have the advantage of reaching regions on the surface that are hard to reach by other application methods. In some cases, vapor may even reach regions that are not reachable to aerosol. Additionally or alternatively, vapor may form a continuous layer more easily than some other application methods, for example, aerosol.

In this context, small particles are particles suitable for forming aerosols. Depending on the particular substance, small particles may have a typical size (for example, radius for quasi-spherical particles or length for elongated particles) of 10 micrometers or less, 5 micrometers or less, and in some cases less than 1 micrometer, for example, between 100 nm and 1000 nm.

The RF absorbance of the treating substance is preferably higher than that of the item to be sanitized. For example, RF dielectric coefficient of most plates (made of clay, glass, or plastic) is about 3-4. Therefore, preferred treating substances may have a dielectric constant greater than 10, more preferably greater than 20. Dielectric loss of most plates is less than 0.01 (for example, the dielectric loss of borosilicate glass, such as Pyrex™, at 1 GHz is about 0.004). Therefore, preferred treating substances may have a dielectric loss greater than 0.1, more preferably greater than 0.5. Dielectric loss is sometimes also referred to as loss tangent or dissipation factor, and these three terms are used interchangeably in this application.

Water has a dielectric constant of about 80 and dielectric loss of about 0.1 (at 1 GHz), but water alone does not form films on most plates and glasses, and thus, may not retain a sufficiently thick layer. Film-forming water may be obtained by adding to water a layer-forming additive, such as small concentration of salt or surfactant. Consistent with some embodiments, such film-forming water may be further improved to increase its viscosity, to increase its dielectric constant and/or loss, and/or to achieve other advantageous properties as discussed below.

In some embodiments, the heating process may be made shorter, and energy consumption lower, by applying a treating substance that absorbs the applied RF energy more efficiently than, for instance, water. This may be associated with having a dielectric constant larger than 80, for example, 90, 100, or 150. This may also be associated with larger dissipation factors, for example, dissipation factors larger than 0.5 or larger than 1. A higher dielectric constant, and even more so, a higher dissipation factor, may result in larger absorption, as well as conversion to heat of a larger portion of the applied energy. The dissipation factor, also known as loss tangent or tan $\delta$, may be approximated by the ratio between the imaginary part and the real part of the complex permittivity of a dielectric material. The lower the electrical conductivity of the material is, the better the approximation may be.

Additionally or alternatively, a treating substance with low heat capacitance, for example, lower than that of water, may be used. With a given amount of absorbed energy, a lower heat capacitance results in a larger temperature increase. Therefore, each of dielectric loss and heat capacitance of the treating substance, either individually or in combination, may help in saving energy.

In some embodiments, the boiling point of the treating substance may be higher than that of water, thus allowing heating the treating substance to higher temperatures than 100° C., for example, 110° C., 120° C., or 140° C., at atmospheric pressure, without boiling. Similarly, having a lower vapor pressure may be an advantage of certain treating substances, because the lower vapor pressure allows for heating to higher temperature before the treating substance is vaporized off the surface. Examples of some desirable values of vapor pressure of a treating substance (at room temperature and atmospheric pressure) are less than 20 mmHg, sometimes, 19 mmHg, 18 mmHg, 15 mmHg, or lower.

Consistent with some embodiments, the treating substance remaining on the surface after sterilization or sanitation or the liquid remaining on the surface after rinsing the treating substance may dried off the item using RF energy.

In accordance with some embodiments, the treating substance is hygroscopic and attracts water molecules from the surrounding. Optionally, the hygroscopicity of the treating substance keeps the surface dry of water, after the treating substance is removed from the surface. The treating substance may optionally be removed by vibrating the item, for example, using sonic and/or ultrasonic waves, and/or by gravity, and/or by blowing air, optionally dry air, on the treating substance.

Examples of some substances, that may be suitable in accordance with some embodiments of the presently disclosed technology include: polyethylene glycol; polypropylene glycol; copolymers of ethylene glycol and propylene glycol; propylene glycol; polysorbates (for example: span 20, span 60, span 80, tween 20, tween 60, or tween 80); polyvinyl alcohol; polyvinyl alcohol copolymers; xanthan gum, metal sulfonates of the general formula M+n(SO3R)–n (where M=Ca, Mg, Zn, or Ti, and R is an alkyl of 6 carbon atoms or more, for example, between 6 and 28 carbons, and for example between 8 and 18 carbon atoms).

Additional examples include: inorganic salts, for example, calcium chloride; metal oxides; silicates; clays, titanates, silicones, alkylene glycol, dimer, trimers, tetramers, olygomers, or polymers of alkylene glycol, glycerol, acylglycerol, diacylglycerol, triacylglycerol, emulsifiers, an colloid (for example, emulsion) of one or more of the above or a solution, for example, an aqueous solution, of one or more of the above.

An exemplary material that has a particular illustrative value may be titanium silicate. Titanium has a high dielectric constant, and silica is hygroscopic. Therefore, their combination in appropriate proportions may result in a treating substance that can be sufficiently heated by RF and sufficiently hygroscopic to enhance after-treatment drying. The exact titanium:silica proportion required for achieving desired performance may be determined by trial and error.

Thus, in accordance with an exemplary embodiment of the disclosed technology, there is provided a method comprising placing an item in an energy application zone, and coating at least a portion of a surface of the item with a layer of a treating substance. The method may further include applying RF energy to the energy application zone such that the treating substance reaches a target temperature, stays at the target temperature for a target duration, and flows off the item. An energy application zone may include any void, location, region, or area where electromagnetic energy may be applied. It may include a hollow, or may be filled or partially filled with liquids, solids, gases, or combinations thereof. By way of example only, an energy application zone may include the interior of an enclosure, interior of a partial enclosure (e.g. conveyor belt oven), interior of a conduit, open space, solid, or partial solid, which allows for the existence, propagation, and/or resonance of electromagnetic waves. The zone may be permanent or may be temporarily constituted for purposes of energy application. For ease of discussion, all such alternative energy application zones may alternatively be referred to as cavities, with the understanding that the term "cavity" implies no particular physical structure other than an area in which electromagnetic energy may be applied. The item may be placed in the energy application zone before, during, or after the coating.

Consistent with some embodiments, the target temperature and target duration are such that the surface of the item is sanitized. Alternatively or additionally, the target temperature and target duration are such that the surface of the item is sterilized.

In some embodiments, after the treating substance stays at the target temperature for the target duration, RF heating is applied to elevate the temperature of the substance to a temperature at which it flows off the surface of the item to significantly decrease the average thickness of the layer.

In some embodiments, applying RF energy comprises heating to a first temperature to achieve sanitizations or sterilization, and thereafter, heating to a second temperature, higher than the first temperature, at which the treating substance flows off the item.

In some embodiments, the treating substance has a viscosity of 15 cS or more at a temperature between 20° C. and 40° C. For example, polyethylene glycol has a viscosity of 40 cS at 24° C., ethylene glycol has a viscosity of 16.1 cPoise or 14.5 cSt at room temperature, and peg 200 has a room temperature viscosity of 50 cPoise or 44 cSt, and each of them may be used as a treating substance or a component thereof according to some embodiments.

In some embodiments, the treating substance has a viscosity of 5 cS or less, optionally 3 cS or less at the target temperature. For example, propylene glycol has viscosity of 3.5 cS at 93° C., and 50% propylene glycol in water has viscosity of 0.95 cS at 93° C.

In some embodiments, the treating substance has a boiling point at least 10° C. higher than that of water, at least at the pressure under which the heating takes place, e.g., an atmospheric pressure.

In some embodiments, the method comprises heating the treating substance to a first temperature, at which the treating substance is applicable by spraying. The method may further comprise applying the treating substance to the item, optionally by spraying, such that the treating substance cools to a second temperature, at which the treating substance clings to the item to form a layer. The method may also comprise applying the RF energy, to sanitize or sterilize the surface of the item.

Consistent with some embodiments of the presently disclosed technology, the treating substance may be selected from an inorganic salt, a metal oxide, a silicate, a clay, a titanate, a silicone, an alkylene glycol, a dimer of an alkylene glycol, a trimer of an alkylene glycol, a tetramer of an alkylene glycol, an oligo(alkylene glycol), a poly(alkylene glycol), glycerol, an acylglycerol, a diacylglycerol, a triacylglycerol, an emulsifier, a colloid (for example, emulsion) of one or more of the above or a solution, optionally an aqueous solution, of one or more of the above. In some embodiments, a solution of a component is a homogeneous mixture of the component in a solvent, wherein the particles of the dissolved components are smaller than about 5 nm. A colloid of a component is a mixture of the component in a dispersing medium, wherein the particles of the component are larger than 5 nm, for example, 200 nm, 1 micrometer, or 5 micrometers.

In an exemplary embodiment, the treating substance comprises an aqueous solution of a water soluble salt. Optionally, the water/salt weight ratio in the solution may be smaller than 1 (i.e. the solution contains more salt than water). An exemplary salt is $CaCl_2$.

In some embodiments, the treating substance comprises an aqueous solution of $CaCl_2$ wherein the water/$CaCl_2$ weight ratio is 2:3 or smaller.

In some methods consistent with embodiments of the disclosed technology, the method comprises rinsing the treating substance after heating. Optionally, after rinsing, RF radiation is applied to dry the item.

In some embodiments, RF radiation may be applied to the item, such that the water fully evaporates when the item temperature is 60° C. or less, or sometimes even 40° C. or less.

An aspect of some embodiments of the presently disclosed technology is directed to a composition of matter useful to one or more of the methods described above. In some embodiments, the composition of matter comprises a solvent, a detergent, and an RF active component. The solvent may be selected from water, alcohols, mixtures of water with one or more alcohols, and mixtures of two or more alcohols. The composition of matter may have one or more of (a) a dielectric constant, for at least one RF frequency, larger than that of the solvent by at least 10%, optionally by at least 20%, and larger than 10, (b) a dielectric loss, for at least one RF frequency, larger than that of the solvent by at least 10%, optionally by at least 20%, and larger than 0.5, (c) a heat capacitance lower than that of the solvent by at least 10%, optionally by at least 20%, (d) a boiling point higher than that of the solvent by at least 10° C., (e) a vapor pressure at 20° C. lower than that of the solvent by at least 10%, and (f) a viscosity higher than that of the solvent by at least 10% at least at a temperatures of 40° C. or below.

In some embodiments, the composition of matter has a viscosity greater than 15 cS at a temperature between 20° C. and 40° C. and/or smaller than 5 cS at temperatures of 60° C. or more.

Examples of RF active components include: inorganic salts, metal oxides, silicates, clays, titanates, silicones, alkylene glycols, dimers of an alkylene glycols, trimers of an alkylene glycols, tetramers of an alkylene glycols, oligo(alkylene glycol), poly(alkylene glycol), glycerol, acylglycerol, diacylglycerol, triacylglycerol, aqueous solutions of one or more thereof, and mixtures of two or more thereof.

In some embodiments, the RF active component includes a salt soluble in the solvent. A component may be considered soluble in a solvent if it has solubility of at least 1 g per liter of that solvent.

In some embodiments, the composition of matter comprises one or more rheology modifiers, for example, xantham gum and/or guar gum.

In some embodiments, the RF active component/solvent weight ratio is larger than 1, that is, the weight of the RF active component in the composition is larger than the weight of the solvent in the composition. For example, the RF active component/solvent weight ratio may be about 3:2.

In some of the above embodiments, the solvent is water, and the RF active component is calcium chloride.

An aspect of some embodiments of the presently disclosed technology is directed to a dishwasher adapted to carry out one or more of the above methods and/or to apply one or more of the above compositions of matter. In some embodiments, the dishwasher comprises an energy application zone, and an RF source, which, in operation, delivers RF energy to the energy application zone. The dishwasher may further comprise a substance applicator for applying a treating substance to a surface of an item, and a controller configured to control the delivery of RF energy such that a treating substance coating an item in the energy application zone would reach a temperature within a predetermined range, such that the entire coating is within the predetermined range.

The dishwasher may comprise a treating substance to be applied by the treating substance applicator, wherein the treating substance is a composition of matter as described herein. In some embodiments, the dishwasher comprises:
an energy application zone;
a substance applicator for applying a treating substance to a surface of an item; and
an RF source, which, in operation, delivers RF energy to the energy application zone; and
a treating substance to be applied by the treating substance applicator,
wherein the treating substance is a composition of matter as described herein.

In some embodiments, the dishwasher may comprise
an energy application zone;
a substance applicator for applying a treating substance to a surface of an item; and
an RF source, which, in operation, delivers RF energy to the energy application zone,
wherein the dishwasher is adapted to carry out a method as described herein.

The dishwasher may comprise a container for the treating substance in flow communication with the substance applicator. Optionally, the container is equipped with at least one of a mixer, for mixing the treating substance with a liquid, and a heater, for aiding in solubilizing the treating substance with a liquid.

An aspect of some embodiments of the presently disclosed technology is directed to a method comprising placing an item in an energy application zone and applying to the item a treating substance to obtain a treated item. The technology may further comprise applying RF energy at the energy application zone such that at least a portion of the treating substance heats to a temperature within a target temperature range, suitable for sanitizing the item. The treating substance optionally has at least one of: (a) a dielectric constant, for at least one RF frequency, larger than that of the solvent by at least 10%, optionally by at least 20%, and larger than 10; (b) a dielectric loss, for at least one RF frequency, larger than that of the solvent by at least 10%, optionally by at least 20%, and larger than 0.5; (c) a heat capacitance lower than that of the solvent by at least 10%, optionally by at least 20%; (d) a boiling point higher than that of the solvent by at least 10° C.; (e) a vapor pressure at 20° C. lower than that of the solvent by at least 10%; and (f) a viscosity higher than that of the solvent by at least 10% at least for temperatures of 40° C. or below.

According to an aspect of some embodiments of the presently disclosed technology, there is provided a device for washing and/or sterilizing an item comprising a substance applicator for coating at least part of a surface of the item with a washing and/or sanitizing and/or sterilizing substance or other material, referred herein as a "treating substance"; a heating unit for heating the treating substance coating the surface of the item to a predefined working temperature (e.g. a sterilization or a temperature above 60° C. or above 70° C. or above 80° C. or between 75-85° C. or higher than 90° C.); and a control unit for controlling the temperature on the coating to at least the working temperature for a predetermined amount of time.

Optionally, the heating comprises EM (electromagnetic) heating, for example, heating by RF. Optionally, the EM heating is combined with cold air and/or hot air and/or dry air (e.g. having a lower water content than ambient air). The air, hot, cold, and/or dry may be used for drying the items after sanitization and/or sterilization.

Additionally or alternatively, the control unit is configured to keep the temperature on the coating equal to or below a predetermined maximal temperature (e.g. below 100° C. or below 90° C. or below 75° C. or even below 65° C.). Thus, in some embodiments, the heating is applied such that the entire coating is within a predetermined temperature range.

In some cases, the item is heated to a temperature and/or duration where a cleaning function is improved or of a required level. Such temperature and/or duration at the temperature may be above or below those desired for sanitization and/or sterilization.

In some cases, a surface treatment other than washing, sanitization or sterilization is desired, for example, setting of a coating, in which the coating is further coated with an energy absorbing layer or the coating is formed integrally with such energy absorbing material.

In some cases, the surface treatment includes a solid state structure treatment in which the crystalline or other solid state structure of an outer layer of an object is modified by heating and/or cooling down provided by controlled heating of the surface layer, for example, in presence of different amount of heating, no heating and/or cooling of other parts of the object. Optionally, the temperature differentials and/or heating time and/or other spatial and/or temporal parameters of the heating profile may be controlled so as to achieve a desired solid state structural effect and/or gradient of effect from the surface into the material.

According to some embodiments, the device further comprises a heating unit for heating the solution before its application to the item. According to some embodiments, the device further comprises a temperature sensor for sensing a temperature on a surface of at least one of said item.

According to some embodiments, the device further comprises a chamber for holding the treating substance. Examples of chambers include solution chamber and aerosol chamber.

According to some embodiments, there is provided a method of washing, sanitizing, and/or sterilizing an item. The method may comprise coating a surface of the item with a washing, sanitizing, and/or sterilizing coating (e.g. solution or aerosol); heating the coating and/or the surface of the item to a working temperature; and controlling the temperature on the coating and/or on the surface to at least the working temperature for a predetermined amount of time.

Optionally, the method further comprises controlling the temperature on the coating not to exceed a predetermined maximal temperature (e.g., below 100° C. or below 90° C. or below 75° C. or even below 65° C.).

Optionally, the method further comprises heating the solution with EM (electromagnetic) heating, which may be RF heating. The heating may be before application of the solution to the item. Additionally or alternatively, the method further comprises heating the solution with electric heating.

According to some embodiments, the solution comprises a salt as an additive to a solvent for forming a conducting solution with high RF absorbance, a higher boiling point, a lower specific heat, a higher viscosity, or any combination thereof. Optionally, the solution comprises a wetting agent. Optionally, the wetting agent is a surfactant.

According to some embodiments, the method further comprises rinsing the coating off the surface of the item after the predetermined amount of time. Optionally, the method further comprises drying the item following the rinsing.

According to some embodiments, the method further comprises sensing a temperature on the surface of the item. In some embodiments, the temperature sensing is with a remote sensor, for example, an IR temperature sensor.

According to some embodiments, the method further comprises including a detergent in the solution.

According to some embodiments, the working temperature is at least 60° C. Optionally, the working temperature is at least 80° C.

According to some embodiments, salt may be used as an additive to a solvent forming a conducting solution with high RF (radio frequency) absorbance, a higher boiling point, a lower specific heat, a higher viscosity, or any combination thereof, for coating a surface of an item. Optionally, the salt is calcium chloride ($CaCl_2$). Optionally, the solvent is water. In some embodiments, the solution has a viscosity greater than 5 centipoises.

According to some embodiments, the solution comprises a rheology modifier. Optionally, the rheology modifier comprises xantham gum. Optionally, the rheology modifier comprises guar gum.

There is provided in accordance with an exemplary embodiment of the disclosure, a device for washing and/or sterilizing an item. The device may comprise a substance applicator for coating at least a part of a surface of said item with a surface treating substance. The device may also comprise a heating unit for heating at least a selected portion of the treating substance coating the part of the surface to a working temperature. The device may also comprise a control unit for controlling the temperature on the coating to at least the working temperature for a time sufficient to provide a desired surface treatment. Optionally, said surface treatment comprises one or more of washing, sanitizing, and sterilization. In some embodiments, the heating comprises electromagnetic (EM) heating, which may be RF heating. In some embodiments, the EM heating is combined with cold air.

In an exemplary embodiment, said control unit is configured to control the temperature on the coating not to exceed a predetermined maximal temperature.

In an exemplary embodiment, said control unit is configured to control the temperature on a selected portion of the coating to exceed a predetermined minimal temperature. In one embodiment, the selected portion is the entire coating.

In an exemplary embodiment, said control unit is configured to control the temperature on the coating to exceed a predetermined minimal temperature at all portions thereof.

In an exemplary embodiment, the device comprises a heating unit for heating the treating substance before its application to said item.

In an exemplary embodiment, the device further comprises a temperature sensor for sensing a temperature on a surface of at least one of said item.

In an exemplary embodiment of the disclosure, the device further comprises a chamber for holding the treating substance.

In an exemplary embodiment, said substance applicator applies said substance to said surface in a form of an aerosol.

There is provided in accordance with an exemplary embodiment a method of surface treating an item. The method may comprise coating a at least part of a surface of said item with a substance and heating at least a selected portion of the treating substance coating the surface of said item to a working temperature. The method may further comprise controlling the temperature on the coating to at least the working temperature for an amount of time sufficient for said surface treatment. The surface treatment may include, for example, sanitization and/or sterilization.

In an exemplary embodiment, the method further comprises controlling the temperature of the treating substance coating the surface of said item so as not to exceed a predetermined maximal temperature.

Optionally or alternatively, the method comprises heating the treating substance with EM heating, which may include RF heating. Optionally, this heating is applied before applying the treating substance to the item. Optionally or alternatively, the method further comprises heating the treating substance with electric heating. Optionally or alternatively, said substance comprises a wetting agent. In an exemplary embodiment, the wetting agent is a surfactant.

Optionally or alternatively, said surface treatment comprises one or more of washing, sanitization, and sterilization and wherein said coating properties and amount are selected to last long enough at said controlled temperature for said surface treatment to occur.

In an exemplary embodiment, said substance comprises a salt as an additive dissolved in a solvent for forming a conducting solution with high RF absorbance, for example, RF dielectric constant higher than 80 and/or RF dielectric loss greater than 0.5 or greater than 1, a higher boiling point, for example, higher than that of the solvent by at least 10%, a lower specific heat and or heat capacitance, a higher viscosity, or any combination thereof.

In an exemplary embodiment, said substance comprises a compound selected from the group consisting of an inorganic salt, a metal oxide, a silicate, a clay, a titanate, a silicone, an alkylene glycol, a dimer of an alkylene glycol, a trimer of an alkylene glycol, a tetramer of an alkylene glycol, an oligo(alkylene glycol), a poly(alkylene glycol), glycerol, an acylglycerol, a diacylglycerol, a triacylglycerol, and an emulsifier. In one embodiment, the substance is combined with a carrier.

In an exemplary embodiment, said coating comprises forming an aerosol comprising said substance and contacting said aerosol with said surface.

In an exemplary embodiment, the method further comprises rinsing the coating off the surface of said item after said predetermined amount of time.

Optionally, the method further comprises drying said item following the rinsing.

Optionally or alternatively, the method comprises sensing a temperature on the surface of said item.

In an exemplary embodiment, the method further comprises including a detergent in said substance.

In an exemplary embodiment, the working temperature is at least 60° C. In an exemplary embodiment, the working temperature is at least 80° C.

In an exemplary embodiment, the treating substance is a liquid having a viscosity greater than 5 centipoises. In an exemplary embodiment, the treating substance is a liquid having a boiling point greater than 100° C.

There is provided in accordance with an exemplary embodiment, a use of a salt as an additive to a solvent forming a conducting solution with high RF absorbance, a higher boiling point, a lower specific heat, a higher viscosity, or any combination thereof, for coating a surface of an item. Optionally, the salt is calcium chloride ($CaCl_2$). Optionally or alternatively, the solvent is water.

In an exemplary embodiment, the solution has a viscosity greater than 5 centipoises.

In an exemplary embodiment, the solution comprises a rheology modifier. Optionally, the rheology modifier comprises xantham gum. Optionally or alternatively, the rheology modifier comprises guar gum.

There is provided in accordance with an exemplary embodiment, a use of a compound selected from the group consisting of an inorganic salt, a metal oxide, a silicates, a clay, a titanate, a silicone, an alkylene glycol, a dimer of an alkylene glycol, a trimer of an alkylene glycol, a tetramer of an alkylene glycol, an oligo(alkylene glycol), a poly(alkylene glycol), glycerol, an acylglycerol, a diacylglycerol, a triacylglycerol, and an emulsifier, for coating a surface of an item with a substance for absorbing RF (radio frequency) radiation.

Optionally, the treating substance is a liquid having a viscosity greater than 5 centipoises. Optionally or alternatively, the treating substance is a liquid having a boiling point greater than 100° C.

There is provided in accordance with an exemplary embodiment a surface treatment system for a temperature based surface treating of an item. The surface treatment system may comprise a cavity, an RF energy applicatory which delivers energy to the cavity, and a coating for an item. The coating has a high RF absorption and is selected to adhere to the item even when heated to said temperature and for a period of time commensurate with said surface treatment.

Optionally, said coating has a low viscosity, when hot, sufficient for one or both of spraying and melting or evaporating at or above a certain temperature after a certain period of time. Optionally or alternatively, said coating has a low toxicity or may be edible.

Unless otherwise specified, all technical and/or scientific terms are used consistently as commonly understood by one of ordinary skill in the art to which the disclosure pertains. Although methods and materials similar or equivalent to those described herein can be used in the practice or testing of embodiments of the disclosure, exemplary methods and/or materials are described below. In case of conflict, the patent specification, including definitions, will control. In addition, the materials, methods, and examples are illustrative only and are not intended to be limiting.

BRIEF DESCRIPTION OF THE DRAWINGS

Some embodiments of the disclosure are herein described, by way of example only, with reference to the accompanying drawings. With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

In the drawings.

DESCRIPTION OF EMBODIMENTS OF THE DISCLOSURE

Figure 1:
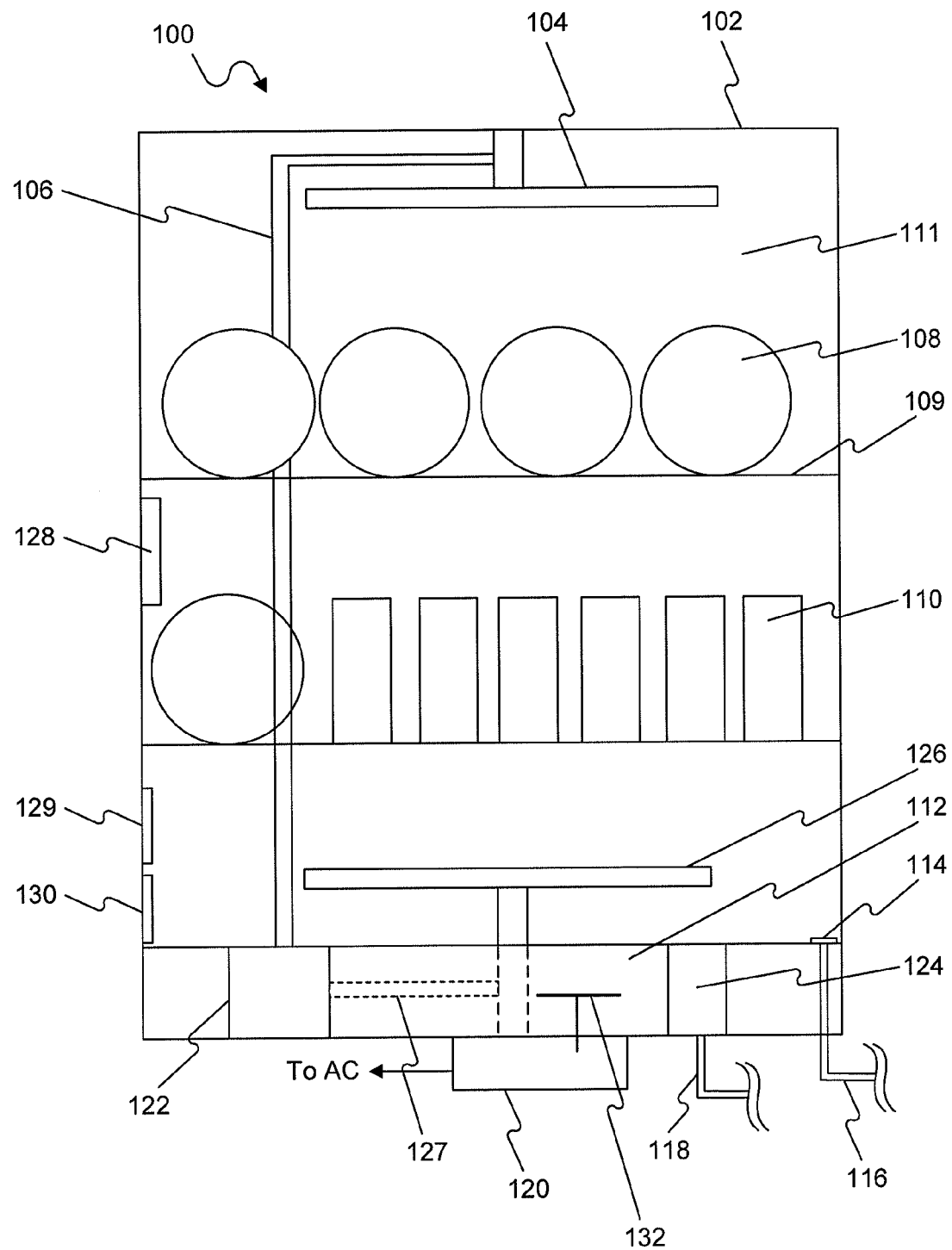
FIG. 1 diagrammatically illustrates an exemplary device for washing food utensils, and for sanitizing and/or sterilizing the food utensils, in accordance with an embodiment of the present disclosure.

The present disclosure, in some embodiments thereof, relates to a device and a method for surface treatment of items, for example, for sanitizing and/or sterilizing items and, more particularly, but not exclusively, to a device and a method for sanitizing and/or sterilizing food utensils including kitchenware, dinnerware, food storage containers, liquid-holding containers, and other items used with products suitable for human consumption and/or medical treatment.

A broad aspect of some embodiments of the disclosure relates to apparatus and method for deploying RF energy with high specificity, especially to surfaces. In an exemplary embodiment of the disclosure, in addition to or instead of spatial and/or temporal and/or material specific control of deposition of RF energy, surface-based specificity is provided.

In an exemplary embodiment, surfaces to be treated are coated with or are otherwise provided with (e.g., manufactured with) an artificial dielectric, to modify the dissipation of RF energy.

In an exemplary embodiment, an object, for example, a medical device or a food holding item is manufactured coated with a dielectric material (or having a coating with dielectric particles therein). Such coating may be used to sterilize and/or otherwise heat the surface of the object one time or more.

In an exemplary embodiment, a cooking implement is provided with such a coated portion (e.g., a surface or inside layer in a pot), and when heated cooks or otherwise heat-treats food or other material placed therein and/or in contact therewith.

In an exemplary embodiment, when an object is coated, in whole or part near a surface or other part thereof to be heated, such coating can be heated, optionally in a spatially selective manner, so as to selectively deposit energy thereat. Optionally, multiple different coatings, with different frequency selectively, are provided, so that each may be separately heated, for example, to a different temperature, for different duration and/or in different order.

In an exemplary embodiment, the coating is provided as a layer beneath a surface. Such a configuration may be useful, for example, if certain other surface properties (e.g., visual properties, adhesion, food-safety) are desired, and/or to prevent overheating of a surface and/or to prevent too sharp temperature gradients in the material. Such gradients may be reduced, for example, by distributing energy absorbing material in a gradually varying spatial profile, rather than as a single sharply demarcated layer. Optionally or alternatively, heat conducting layers and/or elements may be provided to convey heat form the energy absorbing sections to where heating is desired.

In an exemplary embodiment, it may be desired that a hot surface not contact other surfaces, for example, to prevent heat burns or adhesion. Optionally, the coating (if any) is covered by an isolating (coating) layer which optionally does not absorb RF energy or absorbs energy to a lesser extent. Optionally or alternatively, the isolating layer will reduce heat loss to the environment and/or assist in maintaining contact between the energy absorbing layer and the surface. Optionally, the two layers are intermixed, with a higher concentrating of energy absorbing material near the surface to be heated.

In an exemplary embodiment, the insulating coating includes oil or sugar, for example powdered sugar (which melts at 160° C. and up). In an exemplary embodiment, the insulating layer is selected to wash off with the energy absorbing coating (if any) and/or as a separate wash. Other removal methods described herein may also be used.

A potential benefit is that as heating can be surface specific no (or reduced) large volumes of object, water and/or air need to be heated), a lower amount of energy may be used. Therefore, the disclosed process may be more energy efficient than those conventionally used. Similarly, using energy in amount conventionally used, or even a smaller amount, may result in faster heating than using conventional methods.

An aspect of some embodiments relates to surface treating an object by coating at least a part of the object with a material and then heating the material, for example, using RF radiation, so that at least a portion of the surface of the object is heated. For some materials, such as plastic, eddy-current based heating by applying alternating magnetic fields may be used. In another example, a hot material is applied, which hot material adheres to the surfaces. The material may then be maintained at a desired temperature and/or further heated using various methods as known in the art. In an exemplary embodiment, the material is selected so that it can withstand the heating. Optionally or alternatively, the material is applied in amounts that dissipate after a desired amount and/or time of heating are applied. Optionally or alternatively, the material is washed away, for example, using water. In an exemplary embodiment of the disclosure, the surface treatment is washing. Optionally or alternatively, the surface treatment is sanitization and/or sterilization, for example, of food-holding containers or of medical instruments, for example, endoscopes. Different types of objects may have different heating profiles, for example, medical supplies may have a higher temperature and/or duration requirements than food ware. Optionally or alternatively, the object being treated may be limited to a certain maximum temperature and/or duration.

Optionally, the RF heater used can select which spatial portion of a cavity thereof or a spatial portion of the load is to receive more or less (or any) radiation. Optionally or alternatively, selective coating of a part of an object is used to limit surface treatment to that part.

Optionally, the material is viscous enough to remain on the object during heating.

Optionally, the material is applied by dipping or spraying. The application may be manual, mechanical, or automatic.

In an exemplary embodiment, a treatment device is provided including settings for the desired surface treatment (e.g., energy, heat, power, spatial pattern, temporal pattern and/or duration) and/or identification of item to be treated. Optionally, a user can select which material to use as a treating substance and/or at which concentration and/or amount.

Optionally, the device identifies the amount of material inside, for example, based on an amount of power absorption thereby, for example, at particular frequencies.

In an exemplary embodiment, an item to be treated is placed on a tray or cushion which does not absorb RF energy. In some embodiments, the cushion does absorb RF energy, so it heats an item portion in contact with the cushion, for example, an underside of the item. Optionally, the cushion or another holder is designed (e.g., a rack or wire holder) to hold the object in a manner which keeps its surface exposed. Optionally or alternatively, the device includes a treating substance applicator, for example, a directional spray, a spray station and/or a space filling aerosol provider.

In an exemplary embodiment of the disclosure, the material is applied by first wetting an object and then applying a powder or other formulation of the treating substance, with the treating substance adhering to the wet object. In the context of the present disclosure, wetting may be with any suitable liquid, not necessarily water.

For example, the object may be dipped in water or other liquid and then coated with a suitable powder. Either or both of the wetting and material application may be manual or machine provided (e.g., using spraying or immersion). Further, in some embodiments, a user dips items to be treated in a vat of treating substance and then places the wetted items in a device for appropriate heating.

In an exemplary embodiment, the RF heating is combined with heated air and/or other heating means, such as eddy-current based heating. For example, cold, hot, and/or dried air may be used for drying the items after treatment. In this context, dried air may contain less humidity than the air at the vicinity of the item to be dried.

Additionally or alternatively, the control unit is configured to keep the temperature on the coating not to exceed a predetermined maximal temperature.

In accordance with some types of RF heaters, a cavity can be interrogated to determine the type and/or shape and/or number of items therein and/or material coated thereon.

In some cases, heating is applied to a temperature where a cleaning function is improved. Such temperature and/or duration at the temperature may be above or below the desired value for sterilization and/or sanitization. In an exemplary embodiment, a mixture of detergent and/or soap and RF active compound(s) are provided, so that artificial dielectrics for heating are provided. For example, detergent mixtures with silica, alumina, and/or other additive may be used. Optionally, once cleaning is completed, the heat is increased, as long as energy absorbing material remains to heat to a desired temperature, for example, to sterilizing temperature.

Optionally, the treating substance, which may be a dry heating substance, is removed by vibrating the heated items, for example, using sonic or ultrasonic vibrations. Optionally or alternatively, the treating substance is evaporated away. Optionally or alternatively, the heating substance is washed away. Optionally or alternatively, the heating substance, which may be dry, is blown away using air jets.

In some cases, a surface treatment other than washing, sanitizing, or sterilization may be applied, for example, setting of a coating, in which the coating is further coated with an energy absorbing layer or the coating is formed integrally with such energy absorbing material.

In some case, the surface treatment is a solid state structure treatment in which the crystalline or other solid state structure of an outer layer of an object is modified by heating and/or cooling down provided by controlled heating of the surface layer. For example, in presence of different amounts of heating, no heating and/or cooling is applied to other parts of the object. Optionally, the temperature differences and/or heating time and/or other spatial and/or temporal parameters of the heating profile is controlled so as to achieve a desired solid state structural effect and/or gradient of effect from the surface into the material.

An aspect of some embodiments of the present disclosure relates to a substance with one or more of (a) a higher boiling point than water, (b) a higher RF absorbance than water, (c) a lower specific heat than water, and (d) a higher viscosity than water.

The treating substance may be a solid, a liquid, or mixtures thereof. The treating substance may be selected so as to wet a surface (e.g., plastic, ceramic, glass, and/or stainless steel/or polytetrafluoroethylene surface) so as to form a film on the surface. The treating substance optionally has a high dielectric constant (e.g., at least 5, at least 10, at least 20, at least 50, at least 80, at least 90, at least 100). Additionally or alternatively, the treating substance optionally has a high dielectric loss, (e.g., at least 0.5, at least 1, at least 2, or at least 5). Additionally or alternatively, the treating substance is removable (e.g., by washing with water), at least after heating.

The treating substance may comprise, for example, a compound selected from inorganic salts (e.g., chloride salts, bromide salts, and carbonate and bicarbonate salts such as calcium carbonate, magnesium carbonate, sodium carbonate, sodium bicarbonate, potassium carbonate, potassium bicarbonate, metal oxides (e.g., silica, alumina, titania), silicates (e.g., sodium silicate), clays (e.g., kaolinite, montmorillonite, smectite, illite, chlorite), titanates (e.g., barium titanate), silicones, alkylene glycols and dimers, trimers, tetramers, oligomers and polymers thereof, glycerol, acylglycerols, diacylglycerols, triacylglycerols, emulsifiers, aqueous solutions thereof, alcoholic solutions thereof, and mixtures thereof.

According to some embodiments, the treating substance comprises a solid compound (e.g., an inorganic salt, a metal oxide, a silicate, a clay, a titanate) that is applied, for example, as an aerosol, so as to form a solid coating (e.g., a film). The solid may be in the form of small particles, for example, between about 5 and about 20 micrometers, so as to facilitate the application. Solid substances can be removed relatively easily from a surface, for example, by washing with water.

According to some embodiments, the treating substance comprises a liquid (e.g., a silicone, an alkylene glycol, a dimer, trimer, tetramer, oligomer and polymer of an alkylene glycol, glycerol, an acylglycerol, a diacylglycerols, a triacylglycerol) that is applied so as to form a liquid coating (e.g., a film).

In some embodiments, the liquid is selected so as to exhibit (a) a higher boiling point than water, (b) a higher RF absorbance than water, (c) a lower specific heat than water, and/or (d) a higher viscosity than water, at least at temperatures below the working temperature.

A higher boiling point than water refers to a boiling point above 100° C. (at 1 atmosphere). Optionally, the boiling point is above 110° C., 120° C., 140° C., and optionally above 150° C.

In some embodiments, the treating substance comprises one or more silicone oils. Silicone oils may have the formula I:

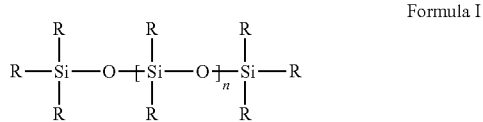

Formula I wherein each R is independently selected from the group consisting of H, alkyl, cycloalkyl, aryl and heteroaryl (e.g., methyl, ethyl, propyl, phenyl), and n is 0 or a positive integer. Examples of silicone oils include polydialkylsiloxanes, polyalkylarylsiloxanes, and polydiarylsiloxanes.

Cyclic silicones, for example, having the formula [—Si(R$_2$)—O—]$_n$, may also be used. In the latter formula, R is defined as above, and n is an integer of at least 3 (e.g., 3-6).

Optionally, silicone oils may be removed by washing with water and a suitable detergent. Alternatively or additionally, a non-polar solvent (e.g., a hydrocarbon or another organic solvent) is used to remove the silicone oil.

In some embodiments, the treating substance comprises an alkylene glycol, an alkylene glycol dimer, an alkylene glycol trimer, an alkylene glycol tetramer, an alkylene glycol oligomer (e.g., 4-10 alkylene glycol units), and/or a poly(alkylene glycol). Optionally, the alkylene glycol is selected from the group consisting of ethylene glycol, propylene glycol and butylene glycol.

The treating substance may optionally comprise a compound having formula II:

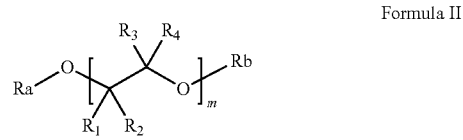

Formula II wherein Ra and Rb are each independently selected from the group consisting of H, alkyl (e.g., $C_{1-4}$ alkyl) and acyl (e.g., $C_{1-4}$ acyl); $R_1$-$R_4$ are each independently selected from the group consisting of H and alkyl (e.g., methyl, ethyl); and m is a positive integer. Thus, for example, the compound of the above formula is an alkylene glycol when m=1, a dimer of alkylene glycol when m=2, a trimer of alkylene glycol when m=3, an oligomer of alkylene glycol when m=4 to 10, and a poly(alkylene glycol) when m>10 (e.g., up to 200).

The compound may comprise different alkylene glycol units. Thus, when m>1 in the above formula, different alkylene glycol units (i.e., the —C($R_1R_2$)—C($R_3R_4$)—O— units) may comprise different groups for any of $R_1$-$R_4$.

In some embodiments, the treating substance comprises glycerol, acyl glycerol, diacyl glycerol and/or triacylglycerol. Optionally, the acyl group(s) attached to the glycerol comprise from 2 to 30 carbon atoms.

Emulsifiers which are suitable for use in embodiments of the disclosure include, for example, polysorbate surfactants (e.g., polysorbate 20, polysorbate, 40, polysorbate 60, polysorbate 65, polysorbate 80), sorbitan surfactants (e.g., Span 20, Span 40, Span 60, Span 65, Span 80), and lecithin.

The liquids described herein are advantageous because they exhibit good wetting properties, high boiling points (e.g., relative to water), large viscosities (e.g. sufficient to limit the running of the treating substance on a vertical surface of the item, such that a sufficiently thick layer of the treating substance remains on the item at least until the desired cleaning level is achieved), and adequate RF absorption. The overall RF absorption of the liquids described herein may be increased further by one or more additive that has good RF absorption, for example, a solid compound described herein (e.g., a titanate, titania, or a silicate).

Alkylene glycols and the abovementioned compounds derived therefrom, such as emulsifiers, glycerol, acylglycerols and diacylglycerol, are also easily removable, for example, by washing with water.

According to some embodiments, the treating substance comprises a liquid (e.g., water) whose normal boiling point is increased by dissolving an additive in the liquid to form a solution and/or an emulsion with one or more of (a) a higher boiling point, (b) a higher RF absorbance, (c) a lower specific heat and/or (d) a higher viscosity.

Together with the liquid, the additive may form a conducting solution with high RF absorption. Soluble salts (e.g., an inorganic salt) such as halide salts are suitable for such embodiments. In the case of water as a liquid or solvent, suitable salts include one or more of lithium chloride, lithium bromide, calcium chloride, calcium bromide, magnesium chloride, sodium nitrite, potassium nitrite, and a variety of other water-soluble inorganic salts. The specific absorption rate (SAR) of RF radiation of the mixture may be controlled by varying the additive concentration. For the purposes of this disclosure, aqueous salt concentrations of 40 to 70% (by weight) in an operative temperature range of 40-90° C. have been found to be effective. Optionally, ionic materials and/or fluids may be used as an additive, in lieu of, or in addition to, the suitable salts.

Other polar solvents that may be used instead of water include ethyl alcohol, acetone, and the like. However, the distinctive odor of these solvents may make them less attractive than water in some embodiments. It is found that the polarity of the solvent may also contribute to the SAR of the mixture, insofar as the dipole moments of polar molecules give rise to rotation in RF electric fields.

Additionally or alternatively, the mixtures disclosed herein may have a lower specific heat than that of the liquid. Pure water has a specific heat of 1 cal/° C./gm, whereas some exemplary mixtures described above may typically have specific heats of 0.5 cal/° C./gm or less. Thus, the temperature increase per calorie of absorbed heat is twice as great in the mixture as in pure water of equal mass.

In some embodiments, the phase transitions, such as evaporation of the liquid (in the working temperature range), may be reduced as much as possible, so as to minimize heat losses and energy consumption. In such cases, the mixture may have a boiling point which is significantly higher than the maximum operative temperature. For example, a 50% calcium chloride solution in water boils at 130° C. and a 60% calcium chloride solution in water boils at roughly 144° C. (at standard conditions), both of which may be used to achieve a final temperature above 100° C. on the item being treated without causing a phase transition.

In some embodiments, the treating substance is applied using a suitable carrier (e.g., a liquid carrier). For example, a solid substance described herein may be applied in the form of a suspension or a colloid (e.g., containing graphite powder or carbonyl iron powder, both of which have high absorption rate of RF radiation), the treating substance being suspended in the carrier, or as a solution of the solid substance in the carrier. A liquid substance described herein may be applied in the form of a solution comprising the treating substance and the carrier, or as an emulsion of the treating substance dispersed in the carrier.

In some embodiments, the treating substance is dispersed in the carrier as a suspension or emulsion. A carrier is selected such that the treating substance is not soluble or miscible in the carrier. For example, a hydrophobic carrier may be selected for a hydrophilic substance, and vice versa. An emulsifier may be used to stabilize a suspension or emulsion. Optionally, the treating substance is dispersed at a concentration of 0.1-50% by weight, and optionally 0.5-20% by weight.

Optionally, the carrier is volatile (e.g., having a boiling point below 80° C.), such that the carrier evaporates shortly after application of the treating substance.

When the treating substance comprises solid particles, the carrier may be selected so as to wet the particles sufficiently so as to facilitate their adhering to the surface and to one another, to thereby form a stronger coating (e.g., a film).

In some embodiments, the carrier is selected to be suitable for forming aerosol droplets comprising the treating substance. A suitable propellant may be used to form an aerosol.

In exemplary embodiments, a dispersion comprises 1-2% (by weight) barium titanate or a carbonate salt (e.g., calcium carbonate) in ethanol. A propellant is used to form aerosol droplets containing the barium titanate or carbonate salt. After a surface is coated with a layer of the dispersion, the ethanol evaporates, leaving a thin and relatively uniform coating of the barium titanate or carbonate salt. At times, it may be desired that the treating substance would adhere to a-non horizontal surface of items at all temperatures up to and including the desired sanitization or sterilization temperature. In such cases the treating substance may have a high viscosity, typically greater than 5 centipoises within the operative temperature range. For calcium chloride in water solutions, this may be achieved by using concentrations of 50% and above. At times, it may be beneficial to add a rheology modifier (to a calcium chloride/water solution or any other solution), such as polyethylene glycol (PEG), guar gum, xanthan gum, edible fibers, or the like. At times, concentrations of 3% (by weight) or less of the rheology modifier may be sufficient to produce the desired viscosity.

At times it may be preferred that the liquid, additive and their solution be non-toxic or of low toxicity to humans.

Dissolving the additive in the liquid may include the use of heating. In some embodiments, heating is applied to the additive and then the additive is mixed into the liquid. Optionally, the additive is mixed with the liquid and the mixture is heated to form a solution. Additionally or alternatively, the additive and the liquid are mixed until the additive dissolves.

Optionally, a substance described herein is stored as a solid at room temperature and pressure, or optionally in any other temperature and/or pressure condition in which the form of the treating substance is that of a solid, and is heated to form a liquid for applying as a coating.

In some embodiments, the treating substance is used to coat surfaces of objects which are to be heated to a minimum 60° C. (or even a minimum of 80 or 90° C.) for heating, sanitizing, sterilizing and/or cleaning the surfaces. The mixture may be applied to the item by a solution applicator such as a spray nozzle or any other means for producing a layer (or film) on the surface of the item. The coat may be a thin film or a thick film. Optionally, the item may be dipped into the solution.

At times, when the treating substance comprises a liquid, the thickness of the coat may be such that the desired minimum temperature is reached before the liquid evaporates.

Optionally, the surfaces may be heated to a temperature above 40° C., above 60° C., above 80° C., above 100° C. or more. Heating may include the use of electromagnetic heating as described in WO2007/096878 titled "Electromagnetic Heating" which relates to an electromagnetic heater for heating an irregularly shaped object, including: a cavity within which an object is to be placed; at least one feed which feeds UHF or microwave energy into the cavity; and a controller that controls one or more characteristics of the cavity or energy to assure that the UHF or microwave energy is deposited uniformly in the object with +30% over at least 80% of the volume of the object. The publication is incorporated herein by reference in its entirety. Additional references that disclose RF techniques which may be useful in some implementations of the present application include PCT/IL09/001,057 and PCT/IL09/001,058, (published as WO/2010/052723 and WO/2010/052724, respectively). The disclosures of these two references are also incorporated herein by reference. For convenience hereinafter, the term "EM heating" may be used for electromagnetic heating as described in any one or more embodiments of the above mentioned WIPO publications. Use of EM heating, as referenced above, may allow for heating surfaces of metal items with EM waves, as arcing phenomena in the metal, which generally occurs in the use of microwaves, can be reduced or eliminated.

In an experiment carried out by the inventor(s), 60 grams of anhydrous $CaCl_2$ (additive) and 40 grams of water (liquid) were mixed and heated to 140° C. (a 60% weight/weight solution was formed). The solution was allowed to cool to about 85-90° C. where it remained a clear liquid. When the solution was applied to a plate, the solution was further cooled to about 80° C. (at which temperature the solution became solid-like) to form a film on the plate. The plate was then exposed to EM irradiation in a device constructed according to an embodiment of the above mentioned WO2007/096878, operating at 600 W, and the solution's temperature was measured in the device using an infrared temperature sensor. The heating was terminated when the solution's temperature increased at a rate of about 10° C./sec to a temperature exceeding 100° C., and the solution on the plate surface became clear and liquid. Results showed that at 80° C. or higher the additive was completely dissolved in the solution.

In a supplementary experiment, the same solution was combined with xanthan gum until the thickness of the solution was such that a thin film applied to the plate remained in place, even when the plate was vertical, at a range of temperatures up to at least 110° C. The mixture remained soft and easily washable with a light rinse.

A further aspect of some embodiments relates to a device and a method for washing, sanitizing, and/or sterilizing items (e.g. food utensils), wherein a coating of the treating substance is applied to the surfaces of the items and heated to a desired sanitization or sterilization temperature. For example, the desired temperature may be 80° C. Optionally, the desired temperature may be 60° C. or higher, 80° C. or higher, 100° C. or higher, 120° C. or higher. Potential benefits of such a device and method may include reductions in a cost of heating relatively large amounts of water as a lower preheating temperature and/or less quantity may be needed for washing. Consistently herein, water used for washing the food utensils may be referred to as "wash water". In some embodiments of the present disclosure, the device may include or be included in a domestic dishwasher. Additionally or alternatively, the device may include or be included in an industrial dishwasher.

In some embodiments, a cleaning agent may be used (with the additive) in order to assist in cleaning of the items. In such cases, the method may be modified to perform a cleaning step. The cleaning agent may comprise one or more alkaline builders and/or one or more wetting agents.

Alkaline builders supply alkalinity for the cleaner. High-alkalinity products may saponify fats and vegetable oils into soluble soaps. Alkaline builders, for example, alkaline salts, may also neutralize acidic contaminants and aid in dispersing oils. Caustics (KOH, NaOH), are highly alkaline (pH 12 to 14), and they saponify fats and work with surfactants to disperse contaminants. Silicates provide medium alkalinity (pH 11 to 12.5) and contribute to detergency. Phosphates have slightly lower alkalinity values (pH 9.5 to 11.5) and provide more detergency than the other builders listed. Mildly alkaline carbonates (pH 9 to 9.5) are mainly used to neutralize acidic contaminants. They also buffer solutions to maintain a specific pH range. The choice of alkaline builder may depend on many factors, including the sensitivity of the items to be washed to the alkaline and user safety.

Wetting agents (e.g. surfactants and synthetic detergents) lower the surface tension of the solution, thereby aiding in removal of contaminants. The wetting agent, in combination with the contaminant, creates an emulsion, thereby preventing re-deposition of the contaminant onto the item being washed. Surfactants have one end that is soluble in water (hydrophilic) and one end that is soluble in oil (hydrophobic). This allows the surfactant molecule to create an oil-water emulsion that is easily rinsed away.

For cleaning, the treating substance is optionally mixed with a cleaning solution, for example, a solution (e.g., an aqueous solution) comprising a cleaning agent. The cleaning solution may optionally be a carrier for the treating substance, as described herein. For example, a solid treating substance described herein (e.g., silica, alumina) may be dispersed in a detergent-containing solution. Alternatively or additionally, the cleaning solution and the treating substance are applied separately.

When cleaning a surface, absorption of RF by the treating substance described herein may heat a surface to which a cleaning solution has been applied, so as to enhance the cleaning efficacy of the solution. Heating may facilitate cleaning in many ways. For example, many detergents are more effective at higher temperatures because micelle sizes are generally smaller at higher temperatures.

The optimal temperature for cleaning will depend on the cleaning solution being used. The degree of heating by RF absorption can be determined accordingly. Optionally, during cleaning, heat is maintained below a level at which the efficiency of the cleaning solution deteriorates, for example, due to damaging the detergent, congealing of proteins in the cleaning solution, or other phase change effects or other chemical processes which may reduce cleaning efficacy.

When sanitizing and/or sterilizing a surface, the temperature must be at least a minimal temperature and at least a minimal period of time necessary for the desired level of sanitization and/or sterilization at that temperature. In an exemplary embodiment, the temperature obtained on a surface by RF heating is optionally at least 80° C., optionally at least 90° C., optionally at least 100° C., optionally at least 110° C., and optionally at least 120° C. A high surface temperature may be obtained efficiently using a small amount of an RF-absorbent substance described herein. The period in which the temperature is maintain may be at least 10 seconds, at least 30 seconds, at least a minute, at least 5 minutes, at least 15 minutes, at least one hour, or shorter or intermediate periods. This may depend, for example, on a required protocol for sterilization. For other surface treatments, a shorter or longer period of time may be targeted.

In some embodiments, a surface is first cleaned using suitable conditions for cleaning, for example, using a cleaning solution and an optimal (or near-optimal) temperature for cleaning, and the cleaned surface is then sanitized and/or sterilized at a suitable temperature, which is usually higher.

In alternative embodiments, cleaning, and sanitization, or cleaning and sterilization are performed in the same step, for example, using a cleaning solution and a temperature which is suitable for both sterilization and cleaning.

In an embodiment of the present disclosure, the RF active additive and the liquid are mixed in the device (with or without the cleaning agent) and then heated, optionally using EM heating, to a predetermined temperature where the additive is dissolved in the solution. Optionally, the solution may be prepared external to the device. Optionally, heating of the solution may be performed using any one of the above mentioned heating methods, or any combination thereof. Optionally, the additive is heated by any one of the above methods, or any combination thereof, and mixed into the liquid.

In some embodiments, the treating substance is recycled. A solid substance may be recycled, for example, by rinsing a surface coated with the treating substance and collecting the solid substance by filtration. An additive in a solution may optionally be recycled by heating the solution once rinsed off the utensils to a temperature where the solvent partly, or entirely, evaporates. A liquid substance with a boiling point higher than that of water may be recycled by heating the treating substance mixed with a rinsing liquid (for example water applied during rinsing) until the rinsing liquid evaporates, and the treating substance remains. Optionally, the treating substance (e.g., a solution) may be recycled by adding any compound (e.g., an additive described herein) that might have been diluted by the rinse liquid, so as to produce the treating substance from the rinse liquid. This may be done in the device itself or outside the device, for instance, in a unit related to the device.

In some embodiments of the present disclosure, a same heating unit for heating the solution additionally heats the wash water. Optionally, a separate heating unit is used for heating the wash water. Additionally or alternatively, waste heat (dissipated heat) from using EM heating and/or other RF heating in the device may be used to heat the wash water and/or the solution. Optionally, a use of wash water is substantially reduced, or possibly eliminated, by using EM heating to dry food residue on the utensils or even to dry the solution and cause them to break up.

It is to be understood that the embodiments described herein are not necessarily intended to limit its application to the details of construction and the arrangement of the components and/or methods set forth in the following description and/or illustrated in the drawings and/or the Examples. The invention may be practiced or carried out in various ways.

Referring now to the drawings, FIG. 1 schematically illustrates an exemplary device 100 (dishwasher) for washing food utensils, shown by exemplary plates 108 and drinking glasses 110, and for sanitizing the food utensils. One or more of the food utensils may be coated by a solution. The solution is as previously described above, and may include a 60% $CaCl_2$ aqueous solution. In the washing steps, the solution would be a washing solution. In an exemplary embodiment, dishwasher 100 includes a housing 102 (with a door, not shown) accommodating one or more item holders, such as racks 109 in an interior cavity 111 for, for example, placing plates 108 and/or drinking glasses 110 (shown from the side) to be washed and/or sanitized. Optionally or alternatively, flatware or pots may be provided.

Figure 3:
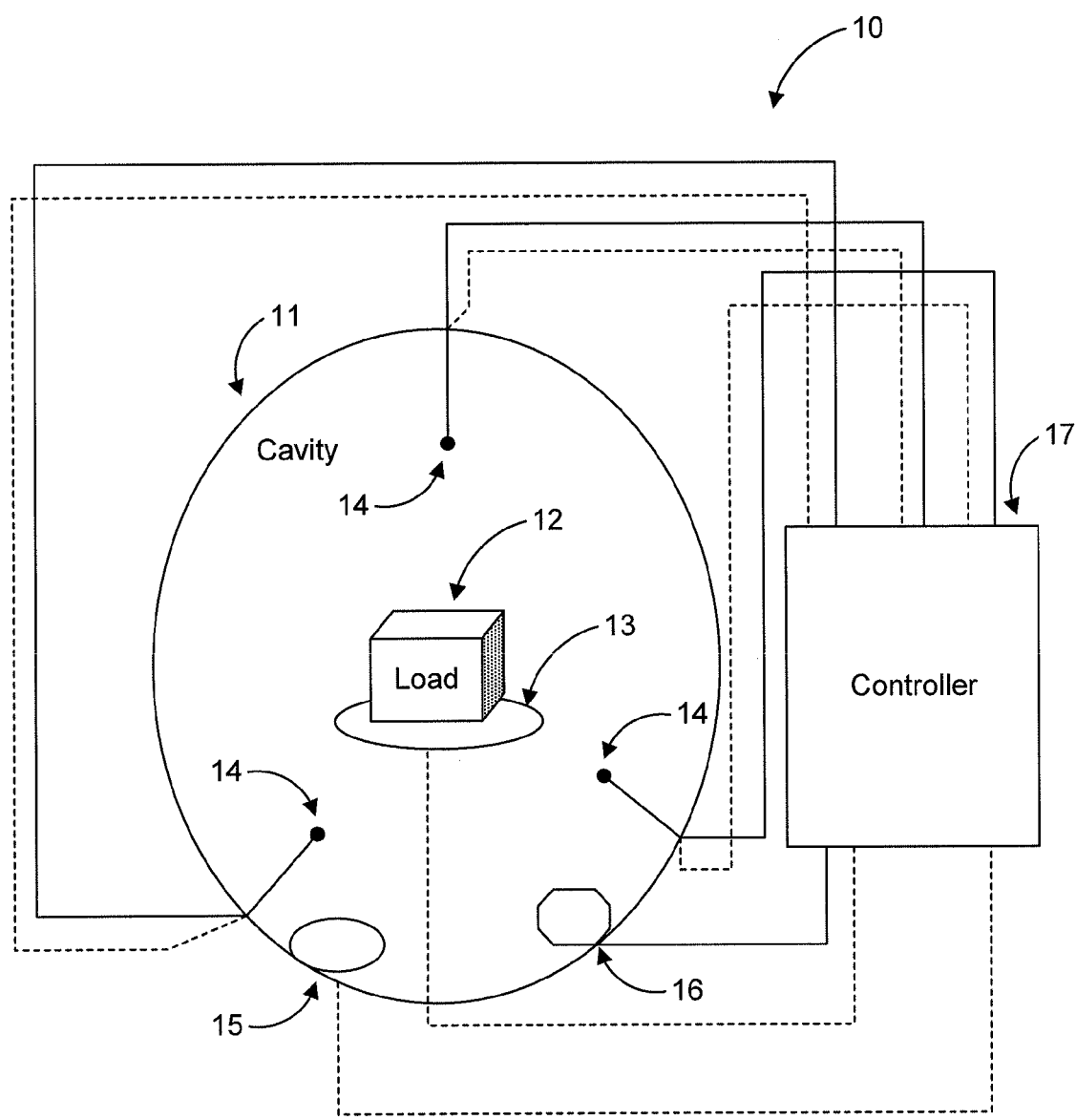
FIG. 3 illustrates an exemplary heating unit for EM heating, in accordance with an embodiment of the present disclosure.

Dishwasher 100 additionally includes a heating unit 112, for example, an RF heater. In an exemplary embodiment of the disclosure, cavity 111 is an RF cavity (e.g., as shown in FIG. 3 below). Optionally, one or more antenna 132 are used to provide RF energy into the cavity.

Optionally, dishwasher 100 includes a substance provider, including, for example, a solution chamber 124 (which may include also cleansing material); a pump 122 for pumping wash water and/or the solution through optional distribution pipes 106 and 127 to a solution applicator for applying the solution coating to the plates and glasses. In one example, the solution applicator comprises an upper spray arm 104 and a lower spray arm 126, respectively. Optionally or alternatively, other spray mechanisms are used, for example, a sprayer adapted to selectively spray only part of cavity 111. In some embodiments, the sprayer may be under control of a camera (not shown), which may use image processing circuitry, to identify items and parts to be treated thereon and guides spraying accordingly.

In some embodiments, solution is applied manually and/or is provided with the items being washed, for example, as a built-in layer.

In an exemplary embodiment of the disclosure, dishwasher 100 includes a control unit 120 which controls a wash cycle and a sanitization cycle and/or other treatments. Control unit 120 may be connected to an external power supply. Alternatively, control unit 120 may include a built-in power supply.

In an exemplary embodiment, dishwasher 100 may include a temperature sensor 129 connected to the control unit. Temperature sensor 129 may be configured to sense the temperature inside housing (air and/or water) and/or to sense the temperature at a surface of one or more of plates 108 and/or drinking glasses 110. In some embodiments, sensing may also be provided by measuring feedback of the RF heater. Dishwasher 100 may further include a fill sensor 130 connected to the control unit. Fill sensor 130 may be configured to sense water level to prevent overflow. Dishwasher 100 may also include an optional detergent dispenser 128; an optional inlet pipe 118 with an intake valve (not shown); and an optional drain 114 connected to an outlet pipe 116.

Optionally, the power supply may be a separate unit in the dishwasher. Optionally or additionally, pump 122 may be a two-way pump for pumping wash water following the wash cycle and/or the solution following the sanitization cycle to outlet pipe 116. Dishwasher 100 may be for domestic use, for commercial use, for industrial use, or any combination thereof. In some embodiments, dishwasher 100 may be, or may be included, in a glass washer. Optionally, dishwasher 100 may be, or may be included, in an under the counter dishwasher. Optionally, dishwasher 100 may be, or may be included, in a hood type dishwasher. Optionally, dishwasher 100 may be, or may be included, in a rack type or tunnel type dishwasher which may include a conveyor. In some embodiments, dishwasher 100 may be, or may be included, in an in-flight type dishwasher. Additionally or alternatively, in the mentioned dishwasher configurations (hood type, rack type or tunnel type, flight type), dishwasher 100 may be a separate unit for sanitization, plates 108 and glasses 110 placed into the dishwasher by a conveyor system, or optionally placed by a user. In some embodiments, cavities for washing in the mentioned dishwasher configurations may include EM cavities suitable for washing, cleaning and sanitization. In some embodiments, dishwasher 100 may be used for medical devices, such as sanitizing bedpans or sterilizing surgical instruments, for example, endoscopes.

In some embodiments, dishwasher 100 may use wash water at relatively low wash temperatures, for example in a range of 10-30° C., optionally 30-70° C., to wash plates 108 and glasses 110, and then use the solution at a user selected sanitization temperature for applying the coating to the plates and glasses for sanitization. In some embodiments, the working (sterilization, sanitization or washing) temperature is predetermined. The working temperature may be 80° C. In some embodiments, the working temperature may be 60° C. or higher, 80° C. or higher, 100° C. or higher, 120° C. or higher. In some embodiments, the wash water is at a minimal temperature required for sanitation, for example, 60° C.

In some embodiments of the disclosure, heating unit 112 may provide EM heating, for example, RF heating, for heating the solution coating the utensils to the working temperature. Heating unit 112 may include one or more feeds (e.g. antennas) for obtaining spectral information from cavity 111, for example, from the surfaces of plates 108 and glasses 110, and/or for transmitting RF energy (e.g. in the range of 700-1100 MHz) to the cavity in order to heat the solution coating the plates and glasses. The feeds may have additional features for EM heating as shown in FIG. 3 and described further on below.

In some embodiments, EM heating is used to dry and break up food particles and or solidified sanitation, sterilization or cleaning solutions on plates 108 and glasses 110, possibly without using wash water.

The debris may, in such cases, be removed by a combination of one or more of gravity, shaking and blown air.

In some embodiments, heating unit 112 may be used to heat the solution for dissolving the additive and optionally a surfactant. Additionally or alternatively, heating unit 112 may heat the wash water. In some embodiments, heating unit 112 may comprise two or three separate heating units, one for heating the wash water to the wash temperature, one for heating the solution to the spraying temperature, and one for heating a solution comprising a surfactant to the spraying temperature. Each of said one or more heating units may provide EM heating, alone or in combination with any other known method of heating. In some embodiments, one or more of the heaters does not provide EM heating. In some embodiments, heating unit 112 may provide RF or microwave heating and/or electrical heating, or any combination thereof.

In some embodiments, the solution is formed in solution chamber 124 where the liquid and the additive (and optionally a surfactant) are combined and optionally heated by heating unit 112 to the temperature at which the additive and surfactant are effectively dissolved in the solution. Water flowing through inlet pipe 118 may be used as the liquid, the amount of water flowing into solution chamber 124 optionally controlled by control unit 120 (opens the intake valve). Optionally, the solution is prepared external to housing 102 and is held in solution chamber 124 for heating by heating unit 112 and/or to be taken by pump 122 for use in spreading the solution (207). A required amount of the additive may be placed inside solution chamber 124 by a user of dishwasher 100 prior to initiating the wash cycle, and/or may be fed into the chamber by automatic or other means. Optionally, the additive in solution chamber 124 is heated to a predetermined temperature by heating unit 112 and then combined with the liquid to form the solution.

Reference is now made to FIG. 3 which schematically illustrates an exemplary heating unit 10 for EM heating, in accordance with an exemplary embodiment. Heating unit 10 may be combined with the features of device 100 to have a heating unit included in the device, similar to that shown in FIG. 1 at heating unit 112. In such cases, heating unit 112 may comprise, within its cavity 11, some or all the elements of device 100. Other elements shown in FIG. 1 (e.g. pump 122, solution chamber 124, upper spray arm 104 and lower spray arm 126 etc.,) are not shown in the figure, but may be included in the combined device.

Cavity 11, which may be similar to cavity 111 shown in FIG. 1 (and provide both the functions of cavity 111 and cavity 11), may be made of a conductor, for example a metal such as aluminum or other conducting material. Optionally, the inner walls of cavity 11 are resistant to the treating substance, and optionally also to wash water. Optionally, the inner walls of cavity 11 are resistant to any chemical that may be used for the cleaning, sanitizing or sterilizing of the treated items, including, for example, detergent and additional chemicals which may be mixed into the wash water and/or into the treating substance. However, it should be understood that the general methodology of the disclosure is not limited to any particular resonator cavity shape. Cavity 11 operates as a resonator for electromagnetic waves having frequencies that are above a cutoff frequency (e.g. 500-1500 MHz or 800-1000 MHZ). The cutoff frequency may depend, among other things, on the geometry of the cavity. Methods of determining a cutoff frequency based on geometry are well known in the art, and may be used.

A load 12, such as the food utensils or other items to be washed, sanitized, sterilized and/or dried, is placed within the cavity, optionally on a supporting member 13 (e.g., racks 109 shown in FIG. 1). In an exemplary embodiment, cavity 11 comprises one or more antennas 14 which may be used for transmitting RF energy into the cavity (e.g. for EM heating). The energy may be transmitted using any method and means known in that art, including, for example, use of a solid state amplifier. One or more, and at times all, of the antennas 14 can also be used one or more times during a sanitization, sterilization, washing and/or drying process for obtaining the spectral information of the cavity within a given band of RF frequencies to determine spectral information from the cavity. For example, in some embodiments, RF radiation of various different frequencies, forming a working band, is delivered to cavity 11, and one or more of antennas 14 are used for estimating the extent to which the radiation at each frequency delivered into cavity 111 is dissipated therein. This information is collected and processed by a controller 17. In some embodiments, controller 17 may be included in control unit 120 shown in FIG. 1. In an exemplary embodiment, cavity 11 also comprises one or more sensors 15. These sensors may provide additional information to controller 17, including, for example, temperature, humidity, etc. The sensed temperature is optionally that at the surface of food utensils 106 and/or 110, which may be sensed, e.g., by one or more IR sensors. Alternatively or additionally, sensor 15 senses the air temperature inside cavity 11, in the vicinity of load 12 (e.g. eating utensils 106 and 110), and/or away from load 12. Sensors 15 may comprise, for example, optic fibers or electrical sensors. Another option is to use one or more internal sensors embedded in or attached to the load (e.g. an optic fiber or a temperature transmitting tag (TTT), as disclosed in WO07/096,878).

In some embodiments, controller 17 is configured to perform a frequency sweep to determine which frequency is absorbed by the load to which extent, and decide, based on this information, how much energy, if any, to transmit using each frequency. For example, controller 17 may be configured to transmit more energy in frequencies that are less dissipated, such that the product of dissipation and delivered energy is substantially constant. Transmitting more energy may be implemented by transmitting with higher power and/or for longer durations. It is also possible to increase the applied energy by delivering less power for much longer durations or more power for much shorter durations. The sweeps may be performed before transmitting RF energy into the cavity, and/or several times during the operation of heating unit 10 in order to adjust the transmitted powers, durations, and frequencies to changes that occur in the cavity during operation.

Additionally or alternatively to frequency sweeping, controller 17 may be configured to perform phase sweeping and to determine the dissipation ratio of different frequency-phase pairs and the energy transmitted in each pair accordingly.

Additionally or alternatively to frequency and/or phase sweeping, controller 17 may be configured to perform amplitude sweeping and to determine the dissipation ratio of different frequency-phase-amplitude triplets and the energy transmitted in each pair accordingly.

Additionally or alternatively, controller 17 may be configured to carry out other sweepings, such as only phase, only amplitude, phase-amplitude pairs, and frequency-amplitude pairs, and determine the amount of energy provided at each such combination of parameters in accordance to the dissipation ratio detected in each combination.

Alternatively or additionally, cavity 11 may include one or more field adjusting elements (FAE) 16. An FAE may include any element within the cavity that may affect the cavity's spectral information or the spectral information derivable from the cavity. Accordingly, an FAE 16 may be for example, any object within cavity 11, including one or more of metal components within the cavity, antenna 14, supporting member 13 and even load 12. The position, orientation, shape and/or temperature of FAE 16 are optionally controlled by controller 17. In some embodiments, controller 17 is configured to perform several consecutive sweeps. Each sweep is performed with a different FAE property (e.g., changing the position or orientation of one or more FAE) such that a different set of spectral information may be deduced. Controller 17 may then select an FAE property based on the obtained spectral information. Optionally, all sweeps may be based on RF energy transmission at intensities that are small enough not to heat the load significantly.

Sweeps, with or without FAE sweeping, may be performed before transmitting RF energy of significant intensities into the cavity, and the sweep may be performed several times during the operation of heating unit 10 in order to adjust the transmitted powers, durations, frequencies, phases, amplitudes (and at times also the FAE property) to changes that occur in the cavity during operation.

In an exemplary embodiment of the disclosure, the FAEs may be controlled and/or load rotated or moved, so that the most useful spectral information is acquired for selective irradiation and/or for setting of radiation parameters. Optionally or alternatively, the load and/or FAEs are periodically manipulated and/or based on a quality or other property of acquired spectral information.

An exemplary transfer of information to the controller is depicted in FIG. 3 by dotted lines. Plain lines depict the control exerted by controller 17 (e.g., the power and frequencies to be transmitted by an antenna 14 and/or dictating the property of FAE 16). The information/control may be transmitted by any means known in the art, including wired and wireless communications. This control information is alternative and/or in addition to other control information discussed herein in connection with one or more of FIGS. 1-2D.

Figure 2A:
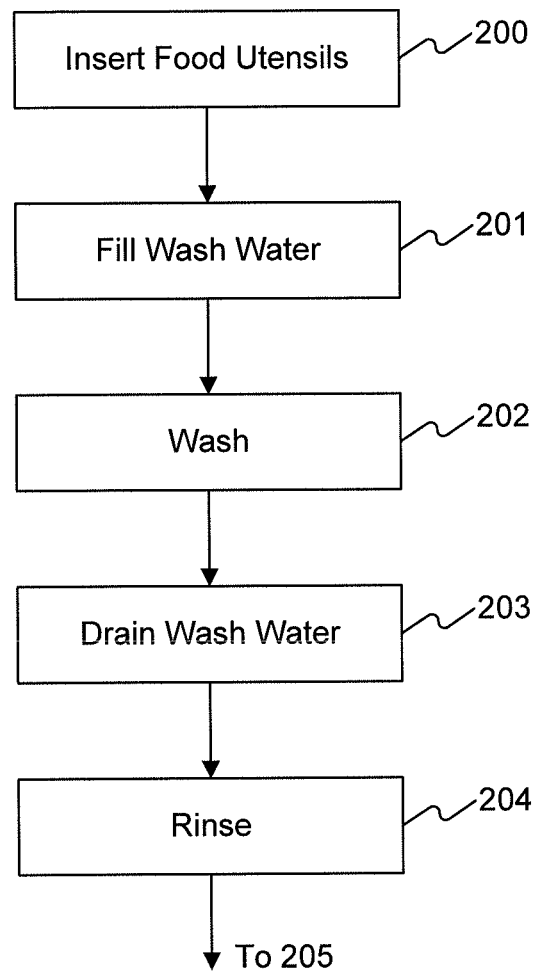
FIGS. 2A and 2B illustrate a flow chart of a wash cycle and sterilization cycle, respectively, in an exemplary method of operation of the device of FIG. 1, in accordance with an embodiment of the present disclosure.
Figure 2B:
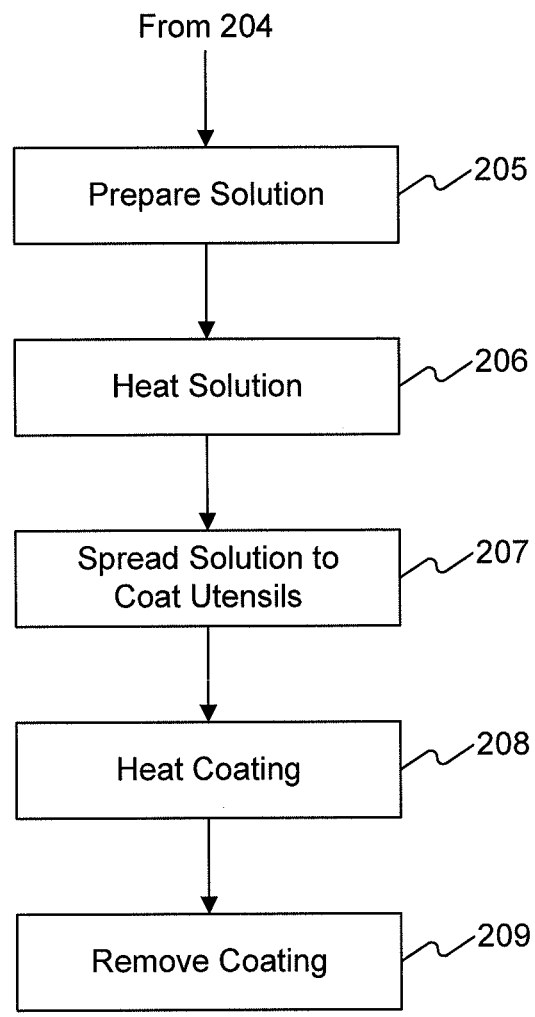

Reference is now made to FIGS. 2A and 2B which illustrate a flow chart of a wash cycle and sanitization/sterilization cycle, respectively, in an exemplary method of operation of dishwasher 100, consistent with some embodiments of the present disclosure. In some embodiments, dishwasher 100 may practice only one of or a combination of two or more of sanitization/sterilization cycle, wash cycle and or drying cycle. At times, a device may perform both sanitization/sterilization and washing as a single cycle (e.g. when the temperature and time affect both cleaning and sanitization/sterilization). The method described is not intended to be limiting in any way, form, or manner and it should be evident to a person skilled in the art that there may be many variations when practicing the method, including at times changes in the order of some steps and/or skipping or making in advance in some of the steps.

At step 200, food utensils, for example plates 108 and glasses 110 are placed on rack 109 inside cavity 111 of housing 102. Detergent is loaded by the dishwasher user in detergent dispenser 128. The additive is loaded by the user in solution chamber 114. The user closes the door and selects wash water temperature and/or sanitization/sterilization temperature. This loading step may be performed for each cleaning cycle or once every several cycles. The temperature information is input to a controller inside control unit 120, or the device is pre-set for a fixed temperature (e.g. to comply with specific laws and regulations)

Steps 201 to 204 optionally take place before the treating substance is applied to the food utensils to clean the utensils before sanitation. Step 205 concerns preparation of the sanitation solution. In some embodiments, this step may be omitted when ready-for-use treating substances are used. Step 206 concerns heating the treating substance and/or its solution before application to the eating utensils. This step may be omitted, for example, if the treating substance is kept or produced (in step 205) at application temperature. In some embodiments, the solution obtained in the preparation step is too hot for use, and the heating applied in step 205 may be replaced by cooling.

At step 201, control unit 120 sends a signal opening the intake valve in inlet pipe 118. Water flows in through inlet pipe 118 in a predetermined amount and is subject to EM heating by heating unit 112 to the wash temperature. Activation of heating unit 112 is controlled by control unit 120. In some embodiments, the water is heated by EM heating or by electric heating or any other means known in the art (including microwave heating). In some embodiments, the water is not heated. In some embodiments, the amount of water may be determined by the user. Control unit 120 sends a signal to detergent dispenser 128 and the detergent is released by the dispenser into the wash water. In some embodiments, the water is stored in a storage tank (not shown) in device 100. Optionally, the quantity of water stored is that required for the wash cycle and/or the sanitization/sterilization cycle. In some embodiments, the water is heated in the storage tank.

At step 202, control unit 120 sends an activation signal to pump 122. Pump 122 propels the wash water (mixed with the detergent) through pipe 106 to upper spray arm 104 and through pipe 127 to lower spray arm 126. The propelled wash water cause upper spray arm 104 and lower spray arm 126 to rotate and spray jets of the wash water at plates 108 and glasses 110.

At step 203, the dirty wash water collects at the bottom of cavity 111 and flows through drain 114 and outlet pipe 116 out of dishwasher 100. In some embodiments, the wash water is pumped by pump 122 to drain 114 (or directly to outlet pipe 116).

At step 204 (optional), rinsing of plates 108 and glasses 110 is done to remove possible residue of food particles and soap on the plates and glasses. Water (without detergent) is pumped by pump 122 and sprayed by upper spray arm 104 and lower spray arm 126. The rinsing water is drained similar to the dirty wash water.

At step 205, the solution is prepared by mixing water with the additive in solution chamber 124. The additive may include high RF absorbing characteristics such as, for example, those found in $CaCl_2$ and/or other treating substances as described hereinabove. The solution may be a 60% aqueous solution of $CaCl_2$. In some embodiment, ready-to-use solution is used, and 205 may be skipped.

At step 206, the solution is heated to a temperature where the additive, and optionally a surfactant, is dissolved in the water. In some embodiments, the temperature may be greater than the sanitization/sterilization temperature. In some embodiments, dissolution of the additive and/or detergent does not require heating, in which case this heating may be omitted. In some embodiments, the heating at 206 is used to decrease the viscosity of the solution, such that it is convenient to apply the hot solution, for example, by spraying, and the hot solution is cooled upon contact with the less-hot food utensils.

At step 207, control unit 120 sends an activation signal to pump 122. Pump 122 propels the heated solution through pipe 106 to upper spray arm 104 and through pipe 127 to lower spray arm 126. The propelled solution causes upper spray arm 104 and lower spray arm 126 to rotate and spray jets of the solution at plates 108 and glasses 110, therefore coating their surfaces.

At step 208, heating unit 112 controls RF heating of the solution that clings to the surface of the food utensils, such that the temperature at the coated surfaces of plates 108 and glasses 110 is at least at the minimum working temperature.

In some embodiments, heating unit 112 maintains or adjusts the temperature on the surface of the food utensils 111, so that the coated surfaces of plates 108 and glasses 110 are at least at the minimum working temperature, or that rate of the heating of said coated surfaces by EM heating is augmented or at least not counteracted by the temperature in cavity 111.

In some embodiments, heating unit 112 maintains the temperature in cavity 111, and/or controls the heating, such that the temperature at the coated surfaces of plates 108 and glasses 110 is below a predetermined maximum temperature being above said minimum working temperature (e.g. to prevent hurting a user that touches the hot dishes and/or in order to prevent damage to the items in the device and or to device or a component thereof, for example in case of items made of a temperature sensitive material, such as plastic).

At step 209, the coating is removed from plates 108 and glasses 110, optionally by rinsing. Alternatively or additionally, the coating removal may be performed by sonication, and/or air blowing. Alternatively or additionally, the coating may be removed by heating to a higher temperature, where it drips off the plates and glasses.

Optionally, coating removal occurs after a predetermined period of time, during which the temperature of the plates and glasses is kept within a predetermined range, to obtain the target cleanliness, for example, sanitation, sterilization, debris break-down and/or release, etc.

In embodiments where rinsing is used, water is optionally pumped by pump 122 and sprayed by upper spray arm 104 and lower spray arm 126. The rinsing water is drained (see step 203). Rinsing water may be cold or pre-heated to any desired temperature.

In embodiments where drying of the eating utensils is required after the coating is removed, heating unit 112 optionally heats the air in cavity 111 to dry plates 108 and glasses 110. Optionally, heating unit 112 provides EM heating directly to water in the cavity, to cause its evaporation without increasing the temperature on the surface of plates 108 and glasses 110 by more than 20° C., or by more than 10° C. or at all. In some embodiments, EM heating may be applied to cause evaporation of water at a low temperature (e.g. 90° C. or less, 60° C. or less, 40° C. or less or even 25° C. or less). This drying may include one or more of the embodiments as described in WIPO publication WO2008/102360 "Drying Apparatus and Methods and accessories for use therewith", incorporated herein by reference in its entirety. This may be assisted by air blown into the device. This air may be at room temperature or pre-heated to any desired temperature. Alternatively or additionally, the air may be dried, for example, by being blown through a desiccant. In some embodiments, the desiccant will be dried by RF heating that evaporates water vapor from the desiccant.

Figure 2C:
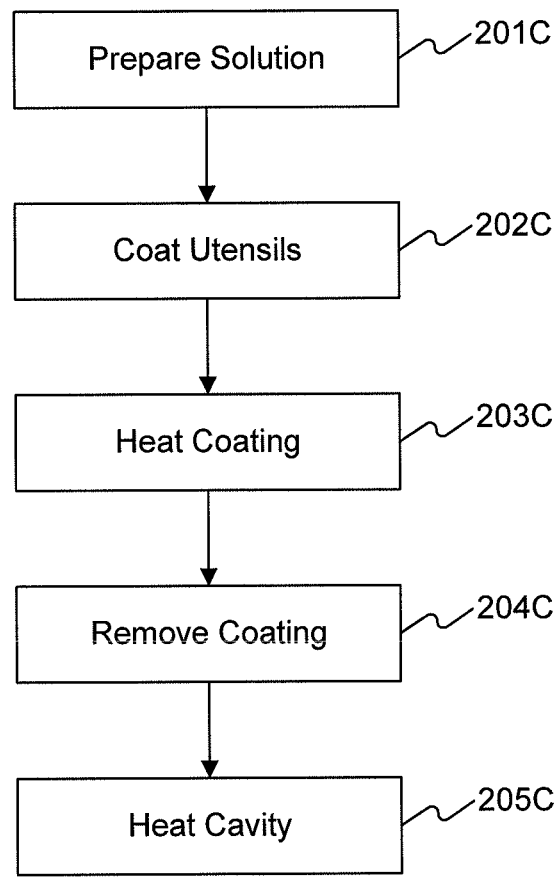
FIG. 2C illustrates a flow chart of an exemplary wash process using the dishwasher shown in FIG. 1, including the use of a surfactant mixed with a solution, in accordance with an embodiment of the present disclosure.

Reference is now made to FIG. 2C which illustrates a flow chart of a three step (optionally four steps) wash process using dishwasher 100 shown in FIG. 1, including the use of a surfactant (and/or other cleaning agent) mixed with the solution, in accordance with an embodiment. In some embodiments, the three step wash process may include a fourth step which includes drying the utensils at the end of the process. The method described is not intended to be limiting in any way, form, or manner, and it should be evident to a person skilled in the art that there may be many variations when practicing the method, including at times changes in the order of some steps and/or skipping or making in advance in some of the steps.

At step 201C, the solution (which may include any solution as described in this application) is mixed with a cleaning agent (e.g., detergent) and/or other wetting agents in solution chamber 124 to obtain a treating substance. Optionally, the mixture is heated by heating unit 112 to a temperature where the additive and the cleaning agent are dissolved in the liquid. In some embodiments, the temperature may be greater than the sanitation and/or sterilization temperature.

At step 202C, the eating utensils are coated with the treating substance. For this, in some embodiments, control unit 120 sends an activation signal to pump 122. Pump 122 propels the heated mixed solution through pipe 106 to upper spray arm 104 and through pipe 127 to lower spray arm 126. The propelled solution causes upper spray arm 104 and lower spray arm 126 to rotate and spray jets of the solution at plates 108 and glasses 110, and thus coating their surfaces at the sterilization temperature.

At step 203C, treating substance coating the surfaces of plates 108 and glasses 110 is heated, optionally by heating unit 112 (e.g. by EM heating) at least to the minimum working (sanitation, sterilization and/or cleaning) temperature. Optionally, heating unit 112 maintains the temperature in cavity 111, or optionally adjusts it, so that the coated surfaces of plates 108 and glasses 110 are at least at the minimum sanitation or sterilization temperature. In some embodiments, heating unit 112 controls the heating such that the surfaces of plates 108 and glasses 110 do not exceed a predetermined maximal temperature. After a predetermined period of time in the cleaning temperature, (which is an amount of time required for the food utensil to be at the sanitation/sterilization temperature, or optionally an amount of time required for the detergent and/or other cleaning agents to act on contaminants on the utensils), the treating substance is optionally removed.

At 204C, the treating substance coating the surfaces of plates 108 and glasses 110 is removed, optionally by rinsing plates 108 and glasses 110 from the plates and the glasses. In some embodiments, water is pumped by pump 122 and sprayed by upper spray arm 104 and lower spray arm 126 for rinsing the treating substance off the food utensils. Rinsing water collects at the bottom of cavity 111 and flows through drain 114 and outlet pipe 116 out of dishwasher 100. Optionally, the wash water is pumped by pump 122 to drain 114 (or directly to outlet pipe 116). Rinsing water may be cold or pre-heated to any desired temperature.

In some embodiments, before the heating substance is rinsed or otherwise removed, it is heated to a higher temperature, for reducing its viscosity and ease its removal. This may be useful, for instance, when the treating substance is too viscous to be efficiently rinsed at the sanitation temperature.

At step 205C (optional), heating unit 112 heats the air in cavity 111 drying plates 108 and glasses 110. Optionally, heating unit 112 provides EM heating directly to water in the cavity, to cause its evaporation without increasing the temperature on the surface of plates 108 and glasses 110 by more than 20° C., or by more than 10° C. or at all. Optionally, EM heating may be applied to cause evaporation of water at a low temperature (e.g. 90° C. or less, 60° C. or less, 40° C. or less or even 25° C. or less). This drying may include one or more of the embodiments as described in WIPO (World Intellectual Property Organization) publication WO2008/102360 "Drying Apparatus and Methods and accessories for use therewith." The publication is incorporated herein by reference in its entirety. This may be assisted by air blown into the device. This air may be at room temperature or pre-heated to any desired temperature.

It should be noted that in this application, the terms "comprises", "comprising", "includes", "including", "having" and their conjugates mean "including but not limited to".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Throughout this application, various embodiments are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Various embodiments and aspects of the present disclosure as delineated hereinabove and as claimed in the claims section below find experimental support in the following examples.

EXAMPLES

Reference is now made to the following examples, which together with the above descriptions, illustrate some embodiments of the disclosure in a non limiting fashion.

In one example, an amount of time or energy needed to reach a sterilization temperature for a solution coating a plate, is calculated. The plate has a radius of 8 cm and is covered by a 1 mm coating of 60% mixture (by weight) of calcium chloride in water. The volume of the mixture is $pi \times (8_{cm}{}^2) \times 0.1_{cm} \sim 20$ cc. The calcium chloride solution has a density of 1.6 gm/cc, so the mass of the liquid layer is $20 \times 1.6 = 32$ gm. The specific heat of the calcium chloride solution is 0.45 cal/° C./gm, so the liquid layer has a heat capacity of $32 \times 0.45 = 14.4$ cal/° C.=60.5 joule/° C. To raise the temperature of the surface film by 30° C. would require only $60.5 \times 30 = 1815$ joules=1.8 kilo-joules, or 1.8 kW-seconds. Thus, for a power input of 0.9 kW, only 2 seconds are needed to heat the plate by 30° C.

In experiments carried out by the inventor(s), $CaCl_2$ dihydrate (additive) was mixed with water (liquid) to reach a mixture of 60 gr anhydrous $CaCl_2$ in 40 gr water. The mixture was subjected to EM heating in a device constructed according to an embodiment of the abovementioned WO2007/096878, operating at 600 W at a frequency range between 800-1000 MHz. The mixture was heated to ca. 140° C., at which temperature the additive had completely dissolved into the water. The solution was then cooled down to about 85° C.-90° C. where it remained a clear liquid, and a thin film coat of this liquid was applied to surfaces of a dinner plate placed inside the oven. The interior of the oven was at room temperature. The coat cooled down to about 80° C. The EM heating was again applied and the solution on the plate is heated at a rate of 10° C. per/sec for about 2 seconds until the temperature of the solution reached over 100° C. Results showed that at a plate temperature greater than 80° C., the additive was completely dissolved in the solution. After sufficient heating, the coat became sufficiently liquid to drip off the plate without the need to add water, leaving only a small residual amount of the solution for a rinsing step.

In another experiment, a 60% $CaCl_2$ solution was combined with xanthan gum until the thickness of the solution was such that a thin film applied to the plate remained in place, even when the plate was vertical, at a range of temperatures up to at least 110° C. The mixture remained soft and easily washable with a light rinse.

In a supplementary experiment, 100 grams of 60% $CaCl_2$ solution in water, heated to melting (80° C.), were combined with 2 grams of guar gum and 1 gram of xanthan gum producing a syrup-like consistency. This syrupy liquid can be allowed to cool to about 60-65° C., before it begins to solidify. Applying the liquid to a plate at a lower temperature, for example, less than 45° C. increases the stickiness. Even if the liquid drips off, a thin coating, of thickness smaller than 1 mm, remains on the plate.

After two minutes in an EM heating device (operating at 900 W), the plate temperature went from 24° C. to 100° C. The device used for EM heating in this experiment was slightly different than that used in the previous experiment, generally providing slower but more uniform EM heating. This hot solution remained as a film on the plate even when heated. Rinsing in cold water removed the solution immediately and left the plate clean.

Using the $CaCl_2$ (dihydrate) powder, 100 grams of a 60% solution is obtained by mixing 79.5 gm of powder with 20.5 gm of distilled water. The reaction is exothermic, raising the temperature of the solution by about 40° C. For improved safety, warm water may be used (<50° C.) rather than boiling water. On the other hand, hotter water brings the benefit of faster dissolving.

In another experiment, the above was repeated with a solution comprising commercially available Jet-Clean™ (NeoDisher) to provide a cleaning agent. This is a water based cleaner comprising cleaning agents, namely: potassium hydroxide, 5% phosphonates, nonionic and amphoteric surfactants, a 60% $CaCl_2$ solution was prepared like in the above first example, except that instead of pure water, Jet-Clean™ was used to dissolve $CaCl_2$, such that the resulting solution comprised 60 gr anhydrous $CaCl_2$ in a 100 gr mixture. This solution was applied to a dinner plate soiled with dried catsup. Upon heating the solution in the above EM heater to 85° C., the catsup exposed to the solution melted, and became easily washable with a light rinse.

Although the disclosure has been made in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A composition of matter comprising:
   a solvent selected from water, alcohols, mixtures of water with one or more alcohols, and mixtures of two or more alcohols;
   a detergent; and
   an RF active component wherein the ratio of the RF active component to the solvent is larger than 1,
   wherein the composition of matter has one or more of
   (a) a dielectric constant, for at least one RF frequency, larger than 10 and larger than a dielectric constant of the solvent by at least 10%;
   (b) a dielectric loss, for at least one RF frequency, larger than 0.5 and larger than a dielectric loss of the solvent by at least 10%;
   (c) a heat capacitance lower than a heat capacitance of the solvent by at least 10%;
   (d) a boiling point higher than a boiling point of the solvent by at least 10° C.;
   (e) a vapor pressure that is lower than a vapor pressure of the solvent by at least 10% at 20° C.; and
   (f) a viscosity that is higher than a viscosity of the solvent by at least 10% at a temperature of 40° C. or below.

2. The composition of claim 1, wherein the composition of matter has a viscosity greater than 15 cS at a temperature between 20° C. and 40° C.

3. The composition of claim 1, wherein the composition of matter has a viscosity smaller than 5 cS at temperatures of 60° C. or more.

4. The composition of claim 1, wherein the RF active component is selected from inorganic salts, metal oxides, silicates, clays, titanates, silicones, alkylene glycols, dimers of an alkylene glycols, trimers of an alkylene glycols, tetramers of an alkylene glycols, oligo (alkylene glycol), poly(alkylene glycol), glycerol, acylglycerol, diacylglycerol, triacylglycerol, and mixtures of two or more thereof.

5. The composition of claim 1, wherein the RF active component is a salt soluble in the solvent.

6. The composition of claim 1, further comprising a rheology modifier.

7. The composition of claim 6, wherein the rheology modifier comprises xantham gum, guar gum or both xantham gum and guar gum.

8. The composition of claim 1, wherein a weight ratio between the RF active component and the solvent is about 3:2.

9. The composition of claim 8, wherein the solvent is water, and the RF active component is calcium chloride.

10. The composition of claim 1, wherein the solvent is water, and the RF active component is calcium chloride.

11. The composition of claim 1, wherein the solvent is water, and the RF active component is calcium chloride.

12. A dishwasher comprising:
    an energy application zone;
    a substance applicator configured to apply a treating substance to a surface of an item in the energy application zone;
    an RF source configured to deliver RF energy to the energy application zone; and
    a treating substance to be applied by the substance applicator,
    wherein the treating substance is a composition of matter according to any one of claims 1 to 7, and 8 to 9.

13. A method, comprising:
    applying a treating substance to an item to obtain a treated item; and
    applying RF energy to an energy application zone containing the treated item such that at least a portion of the treating substance heats to a temperature within a target temperature range suitable for sanitizing the item,
    wherein the treating substance is a composition of matter according to claim 1.

14. The method of claim 13, comprising:
    coating at least a portion of a surface of the item with a layer of treating substance; and
    applying RF energy to the energy application zone, such that the layer of treating substance reaches a target temperature, stays at the target temperature for a target duration, and flows off the item after the target duration.

* * * * *